United States Patent
Sharma

(10) Patent No.: US 12,005,258 B2
(45) Date of Patent: Jun. 11, 2024

(54) MEDICAL SYSTEM FOR THERAPY ADJUSTMENT

(71) Applicant: Medtronic, Inc., Minneapolis, MN (US)

(72) Inventor: Vinod Sharma, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 240 days.

(21) Appl. No.: 17/404,542

(22) Filed: Aug. 17, 2021

(65) Prior Publication Data

US 2022/0032068 A1 Feb. 3, 2022

Related U.S. Application Data

(62) Division of application No. 16/394,942, filed on Apr. 25, 2019, now abandoned.

(60) Provisional application No. 62/663,055, filed on Apr. 26, 2018.

(51) Int. Cl.
| | | |
|---|---|---|
| *A61N 1/365* | (2006.01) | |
| *A61B 5/00* | (2006.01) | |
| *A61N 1/37* | (2006.01) | |
| *A61N 1/372* | (2006.01) | |
| *A61N 1/375* | (2006.01) | |
| *G16H 40/60* | (2018.01) | |

(52) U.S. Cl.
CPC ........ *A61N 1/36514* (2013.01); *A61B 5/0031* (2013.01); *A61N 1/37252* (2013.01); *A61B 5/4836* (2013.01); *A61B 5/686* (2013.01); *A61N 1/3706* (2013.01); *A61N 1/3756* (2013.01); *G16H 40/60* (2018.01)

(58) Field of Classification Search
CPC ........................... A61N 1/3706; A61N 1/3708
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |
| 5,545,186 A | 8/1996 | Olson et al. |
| 5,755,736 A | 5/1998 | Gillberg et al. |
| 6,970,742 B2 | 11/2005 | Mann et al. |

(Continued)

FOREIGN PATENT DOCUMENTS

WO 2017/120560 7/2017

OTHER PUBLICATIONS

Cowie et al., "Development and validation of an integrated diagnostic algorithm derived from parameters monitored in implantable devices for identifying patients at risk for heart failure hospitalization in an ambulatory setting," Mar. 19, 2013, European Heart Journal, 34:2472-2480.

(Continued)

*Primary Examiner* — Brian T Gedeon
(74) *Attorney, Agent, or Firm* — Mueting Raasch Group

(57) ABSTRACT

Methods and systems for seamless adjustment of treatment are disclosed. A determination can be made as to whether to intervene with a patient's treatment based on data obtained from implantable electrodes and/or non-implantable electrodes. The data from non-implantable electrodes have a correction factor applied to adjust for less accuracy compared to data acquired from implantable electrodes.

10 Claims, 17 Drawing Sheets

(56) References Cited

U.S. PATENT DOCUMENTS

| | | |
|---|---|---|
| 7,001,359 B2 | 2/2006 | Rogers |
| 7,008,413 B2 | 3/2006 | Kovach et al. |
| 7,054,782 B2 | 5/2006 | Hartlaub |
| 7,160,284 B2 | 1/2007 | Ullestad et al. |
| 7,264,611 B2 | 9/2007 | Christenson et al. |
| 7,577,475 B2 | 8/2009 | Cosentino et al. |
| 7,986,994 B2 | 7/2011 | Stadler et al. |
| 8,255,046 B2 | 8/2012 | Sarkar et al. |
| 8,439,683 B2 | 5/2013 | Puri et al. |
| 8,585,604 B2 | 11/2013 | Bennett et al. |
| 9,403,019 B2 | 8/2016 | Sambelashvili et al. |
| 9,789,319 B2 | 10/2017 | Sambelashvili |
| 2003/0093125 A1 | 5/2003 | Zhu et al. |
| 2003/0097158 A1 | 5/2003 | Belalcazar |
| 2003/0233132 A1 | 12/2003 | Pastore et al. |
| 2004/0147969 A1 | 7/2004 | Mann et al. |
| 2004/0158293 A1 | 8/2004 | Yonce et al. |
| 2004/0220635 A1 | 11/2004 | Burnes |
| 2006/0009810 A1 | 1/2006 | Mann et al. |
| 2006/0253159 A1 | 11/2006 | Siejko et al. |
| 2006/0276848 A1 | 12/2006 | Min et al. |
| 2007/0167843 A1 | 7/2007 | Cho et al. |
| 2007/0260285 A1* | 11/2007 | Libbus ................. A61B 5/0205 607/9 |
| 2010/0030293 A1 | 2/2010 | Sarkar et al. |
| 2010/0042173 A1 | 2/2010 | Farazi et al. |
| 2010/0113889 A1 | 5/2010 | Ghanem |
| 2012/0032243 A1 | 2/2012 | Kutsukake et al. |
| 2012/0109243 A1* | 5/2012 | Hettrick ................. A61B 5/686 600/509 |
| 2012/0238886 A1 | 9/2012 | Sweeney |
| 2013/0116578 A1* | 5/2013 | An ....................... A61B 5/7275 600/484 |
| 2013/0226011 A1 | 8/2013 | Zhang et al. |
| 2014/0107503 A1 | 4/2014 | Sachanandani et al. |
| 2016/0310031 A1 | 10/2016 | Sarkar |
| 2016/0361026 A1 | 12/2016 | Sarkar et al. |
| 2017/0001005 A1 | 1/2017 | Zhang et al. |
| 2017/0100081 A1 | 4/2017 | Thakur et al. |
| 2017/0245794 A1 | 8/2017 | Sharma et al. |
| 2018/0020937 A1 | 1/2018 | Chou |

OTHER PUBLICATIONS

Fredrickson, "Smart-Sock: Monitoring ankle edema at home," Feb. 2016, Retrieved from https://vcea.wsu.edu/eec2016/smart-sock/ on Aug. 20, 2019, 3 pages.

International Patent Application No. PCT/US2019/29193, filed Apr. 25, 2019; International Search Report/Written Opinion issued Jul. 24, 2019; 18 pages.

Ritzema et al., "Physician-directed patient self-management of left atrial pressure in advanced chronic heart failure," Mar. 9, 2010, Circulation, 121(9): 1086-95.

European Patent Application No. 19793009.2, filed Apr. 25, 2019; Supplementary European Search Report and Opinion issued Feb. 9, 2022; 9 pages.

* cited by examiner

Baseline Cardiovascular Medication Regimen

BASELINE MEDICATIONS

| Drug Class (Cardiovascular Related e.g. Class Medications) | Drug | Dose and units | Frequency | Route | Reason for use (Medical diagnosis or other reason, e.g. Prophylaxis) |
|---|---|---|---|---|---|
| ACE-inhibitor | ☐ Benazepril (Lotensin)<br>☐ Captopril (Capoten)<br>☐ Enalapril (Vasotec)<br>☐ Fosinopril (Monopril)<br>☐ Lisinopril (Prinivil, Zestril)<br>☐ Moexipril (Univasc)<br>☐ Perindopril (Aceon)<br>☐ Quinapril (Accupril)<br>☐ Ramipril (Altace)<br>☐ Trandolapril (Mavik)<br>☐ Other:_____ | | | | |
| Angiotensin Receptor Blocker | ☐ Candesartan (Atacand)<br>☐ Eprosartan (Teveten)<br>☐ Irbesartan (Avapro)<br>☐ Losartan (Cozaar)<br>☐ Telmisartan (Micardis)<br>☐ Valsartan (Diovan)<br>☐ Other:_____ | | | | |
| Beta blocker (also known as Beta-Adrenergic Blocking agents) | ☐ Acebutolol (Sectral)<br>☐ Atenolol (Tenormin)<br>☐ Betaxolol (Kerlone)<br>☐ Bisoprolol/hydrochlorothiazide (Ziac)<br>☐ Bisoprolol (Zebeta)<br>☐ Metroprolol (Lopressor, Toprol XL)<br>☐ Nadolol (Corgard) | | | | |

FIG. 13A

| | | | | | |
|---|---|---|---|---|---|
| | ☐ Propranolol (Inderal) <br> ☐ Sotalol (Betapace) <br> ☐ Other:_____ | | | | |
| Combined alpha and beta blockers | ☐ Carvedilol (Coreg) <br> ☐ Labetalol hydrochloride (Normodyne, Trandate) <br> ☐ Other:_____ | | | | |
| Aldosterone Antagonist | ☐ Spironolactone (Aldactone) <br> ☐ Eplerenone (Inspra) | | | | |
| Electrolyte Supplement(s) | ☐ Potassium <br> ☐ Magnesium | | | | |
| Vasodilator <br> (Also known as Nitrates) | ☐ Hydralazine (Apresoline) <br> ☐ Isosorbide Dinitrate (Isordil) <br> ☐ Nesiritide (Natrecor) <br> ☐ Nitrates <br> ☐ Minoxidil <br> ☐ Other:_____ | | | | |
| Anti-arrhythmic Agent | ☐ Amiodarone <br> ☐ Other:_____ | | | | |
| Calcium Channel Blocker | ☐ Amlodipine (Norvasc, Lotrel) <br> ☐ Diltiazem (Cardizem, Tiazac) <br> ☐ Felodipine (Plendil) <br> ☐ Nifedipine (Adalat, Procardia) <br> ☐ Nimodipine (Nimotop) <br> ☐ Nisoldipine (Sular) <br> ☐ Verapamil (Calan, Verelan) <br> ☐ Other:_____ | | | | |
| Funny Channel (I$_f$) blocker | ☐ Ivabradine (Corlander) <br> ☐ Other:_____ | | | | |
| Digitalis Preparation <br> Also known as Digoxin and Digitoxin | ☐ Lanoxin <br> ☐ Other:_____ | | | | |
| Other | ☐ Other:_____ <br> ☐ Other:_____ | | | | |

FIG. 13B

| Diuretic Regimen | | | | |
|---|---|---|---|---|
| Medication<br>(Cardiovascular Related<br>e.g. Class Medications) | Frequency | Route | Titration Stipulations<br>Initiate PRN if baseline<br>dose recently adjusted? | |
| BASELINE Diuretic:<br>☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide<br>    (Esidrix, Hydrodiuril)<br>☐ Indapamide (Lozol)<br>☐ Spironolactone (Aldactone)<br>☐ Other:_____ | | | | |
| BASELINE Diuretic:<br>☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide<br>    (Esidrix, Hydrodiuril)<br>☐ Indapamide (Lozol)<br>☐ Spironolactone (Aldactone)<br>☐ Other:_____ | | | | |
| BASELINE Diuretic:<br>☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide<br>    (Esidrix, Hydrodiuril)<br>☐ Indapamide (Lozol)<br>☐ Spironolactone (Aldactone)<br>☐ Other:_____ | | | | |

FIG. 14

| Diuretic Regimen for Intervention | | | | |
|---|---|---|---|---|
| Medication (Cardiovascular Related e.g. Class Medications) | Frequency | Route | Titration Stipulations Initiate PRN if baseline dose recently adjusted? | |
| Round 1 PRN:<br>Diuretic<br>☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide (Esidrix, Hydrodiuril)<br>☐ Indapamide (Lozol)<br>☐ Spironolactone (Aldactone)<br>☐ Other:_____<br>And/Or<br>Vasolidilator<br>☐ Hydralazine (Apresoline)<br>☐ Isosorbide Dinitrate Isordil)<br>☐ Nesiritide (Natrecor)<br>☐ Nitrates<br>☐ Minoxidil<br>☐ Other:_____ | RN x 3 days | | ☐ Yes | ☐ No: if baseline dose adjustment made within last ____ days<br><br>Comment:____<br>_____<br>_____<br>_____ |
| Round 2 PRN:<br>Diuretic<br>☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide (Esidrix, Hydrodiuril) | RN x 3 days | | ☐ Yes | ☐ No: if baseline dose adjustment made within last ____ days<br><br>Comment:____<br>_____<br>_____ |

FIG. 15A

☐ Indapamide (Lozol)
☐ Spironolactone (Aldactone)
☐ Other: _____

And/Or Vasodilator
☐ Hydralazine (Apresoline)
☐ Isosorbide Dinitrate (Isordil)
☐ Nesiritide (Natrecor)
☐ Nitrates
☐ Minoxidil
☐ Other: _____

FIG. 15B

MEDICAL SYSTEM FOR THERAPY ADJUSTMENT

CROSS-REFERENCE TO RELATED APPLICATIONS

This present application is a Divisional application of U.S. patent application Ser. No. 16/394,942, filed Apr. 25, 2019, which claims priority to, and the benefit of, U.S. Provisional Patent Application Ser. No. 62/663,055, filed on Apr. 26, 2018, the entire contents of which are hereby incorporated by reference.

TECHNICAL FIELD

The present disclosure relates to a medical system, and, more particularly, to a medical system configured to determine whether to intervene with a patient's treatment.

BACKGROUND

Chronic heart failure (CHF) is a serious condition that occurs when a heart is unable to consistently pump blood at an adequate rate. To improve the ability of the heart to efficiently pump blood, CHF patients may require an implantable medical device (IMD). IMDs such as implantable cardioverter defibrillators (ICDs) or pacemakers are capable of delivering cardiac resynchronization therapy for improving a CHF patient's heart function. Despite using IMDs to improve heart function, CHF patients may progressively deteriorate, as evidenced by weight gain, change in blood pressure, malaise, fatigue, swelling in legs and feet, fainting, and/or palpitations.

Patient data are obtained in a variety of ways. Typically, a patient directly conveys health data to medical personnel during an office visit. Some data may be automatically generated and sent over the Internet to a computer system or health care system. For example, electronic weight scales are configured to weigh a patient and then automatically transmit that data to the health care system.

In response to the collected data, healthcare systems can respond in a variety of ways. Some healthcare systems are able to generate health alerts based upon data detected by an IMD. One exemplary healthcare system relates to US Patent Application US 2010-0030293 A1 to Sarkar et al. that is capable of generating alerts for a patient to seek medical treatment in response to detected information. For example, a medical device may detect worsening heart failure in the patient based on a diagnostic parameter. Upon detecting worsening heart failure, the medical device may, for example, provide an alert that enables the patient to seek medical attention before experiencing a heart failure event.

While numerous healthcare systems are able to automatically notify health care workers of potential health issues such as that which is described in US Patent Application US 2010-0030293 A1 to Sarkar et al., a healthcare system typically requires a physician's input to adjust therapy (i.e. medication) delivered to a patient. It is desirable to develop a healthcare system that is able to seamlessly respond to a patient's deteriorating health conditions without directly contacting a physician.

SUMMARY OF THE DISCLOSURE

Methods and systems are disclosed for managing therapy delivered to a patient. One or more embodiments comprise a system that includes an implantable medical device comprising one or more electrodes configured to be implanted within a patient's body, to acquire first signals corresponding to signals sensed from within the patient's body and to generate first data transmissions in response to the acquired first signals. The system further includes a wearable device comprising one or more electrodes is configured to be positioned in contact with an external surface of the patient's body, to acquire second signals corresponding to signals sensed from the external surface of the patient's body, and to generate second data transmissions in response to the acquired second signals. The system further includes an input/output device that is configured to receive the first data transmissions and the second data transmissions. The system also includes one or more processors that are configured to: (1) receive the first data transmissions and the second data transmissions, (2) compare the received first data transmissions and the received second data transmissions to one or more thresholds, (3) determine whether data of the received first data transmissions and the received second data transmissions is indicative of a heart failure (HF) worsening episode based on the comparing, and (4) adjust a patient's therapy in response to the HF worsening episode being indicated.

BRIEF DESCRIPTION OF DRAWINGS

FIGS. 13A and 13B are a diagram depicting an exemplary baseline cardiovascular medication regimen, e.g., for use in the exemplary symptom management intervention process of FIG. 4.

FIG. 14 is a diagram depicting an exemplary baseline diuretic regimen, e.g., for use in the exemplary symptom management intervention process of FIG. 4.

FIGS. 15A and 15B are a diagram depicting another exemplary baseline diuretic regimen, e.g., for use in the exemplary symptom management intervention process of FIG. 4.

DETAILED DESCRIPTION

Exemplary systems, methods, and interfaces shall be described with reference to FIGS. 1-12. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 1:
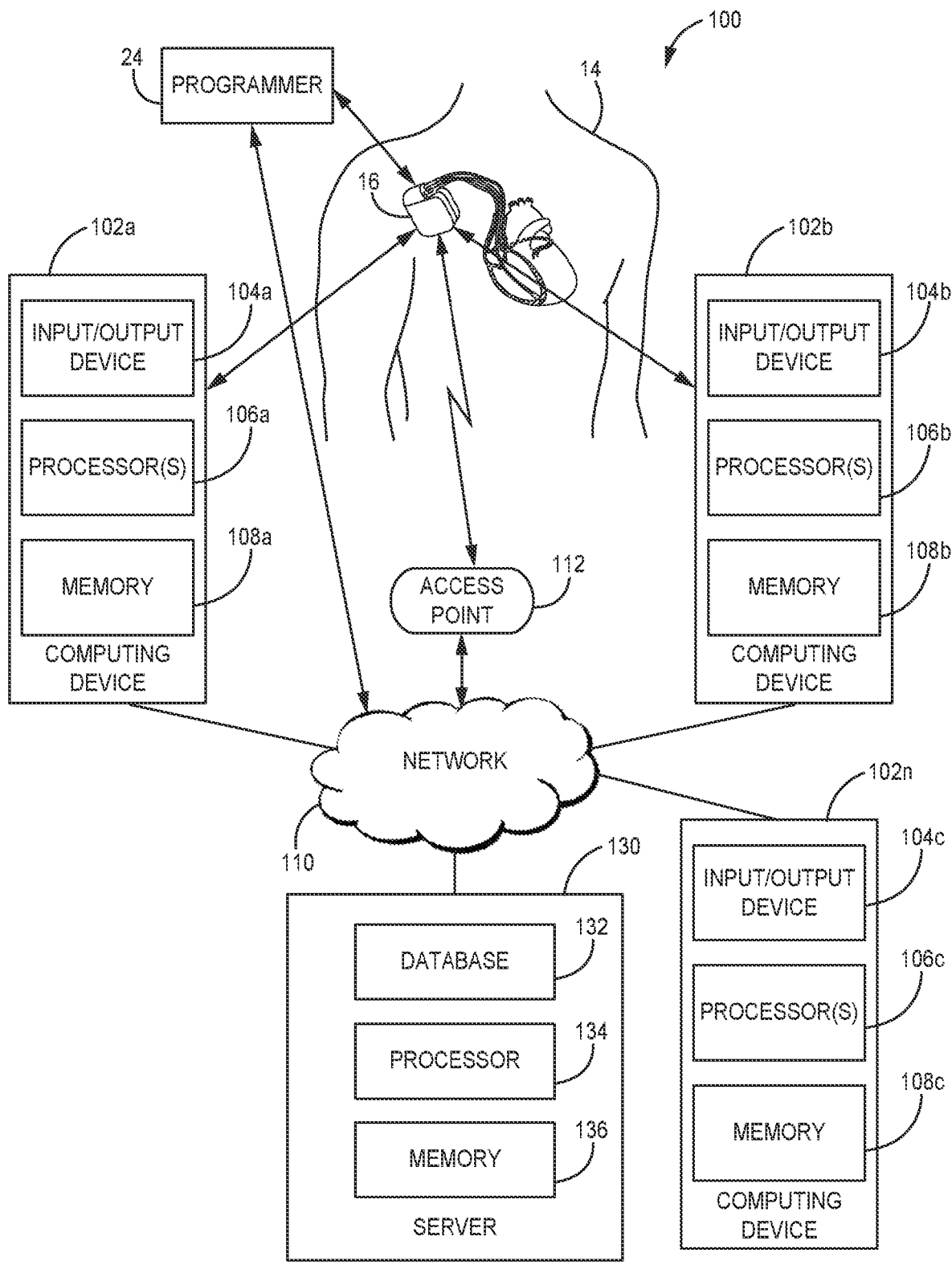
FIG. 1 is a block diagram illustrating an example computer system that includes an external device and one or more computing devices that are coupled to the IMD and programmer shown in FIG. 1 via a network.
Figure 2:
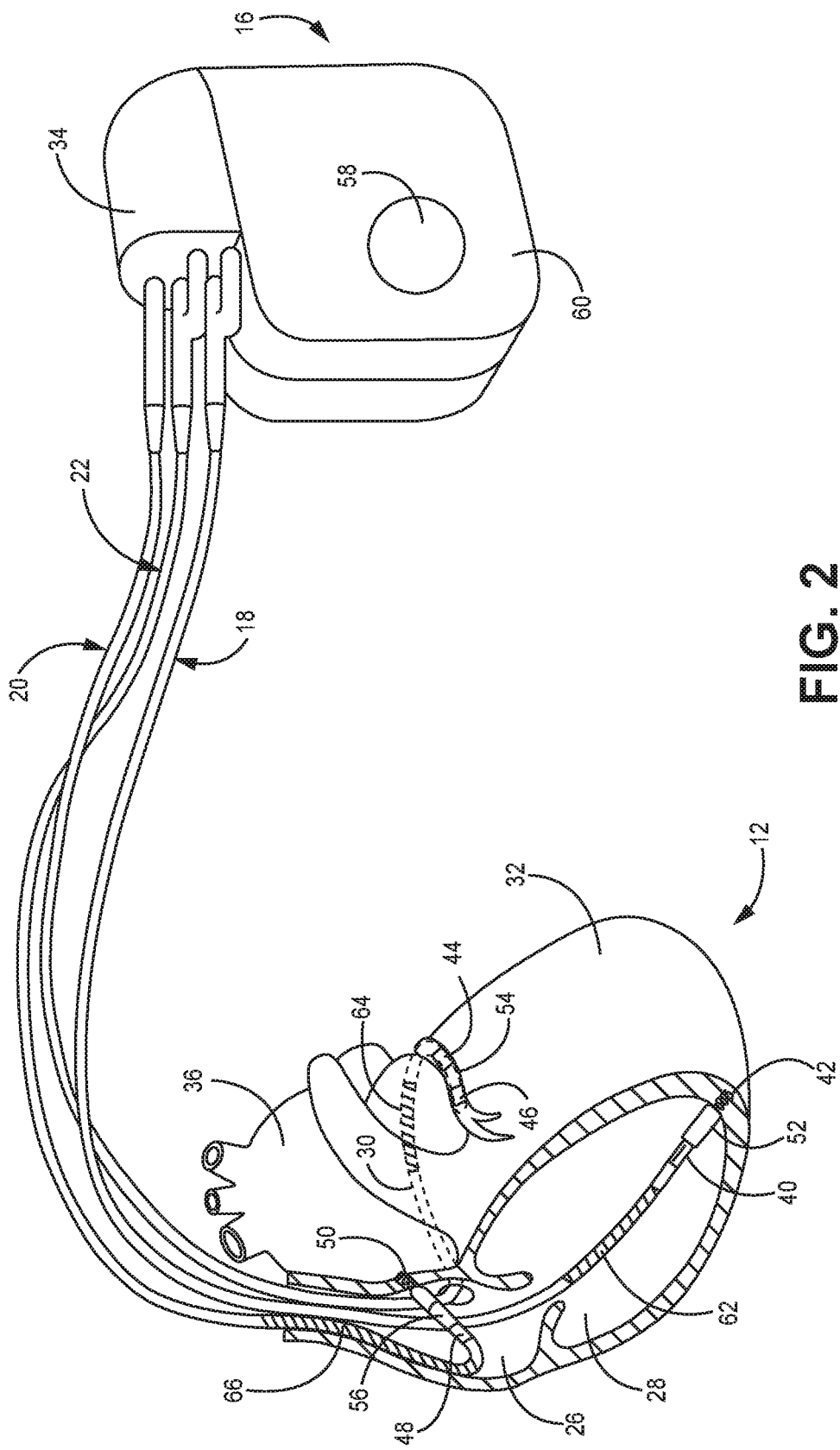
FIG. 2 is a diagram of the exemplary IMD shown in FIG. 1.
Figure 3:
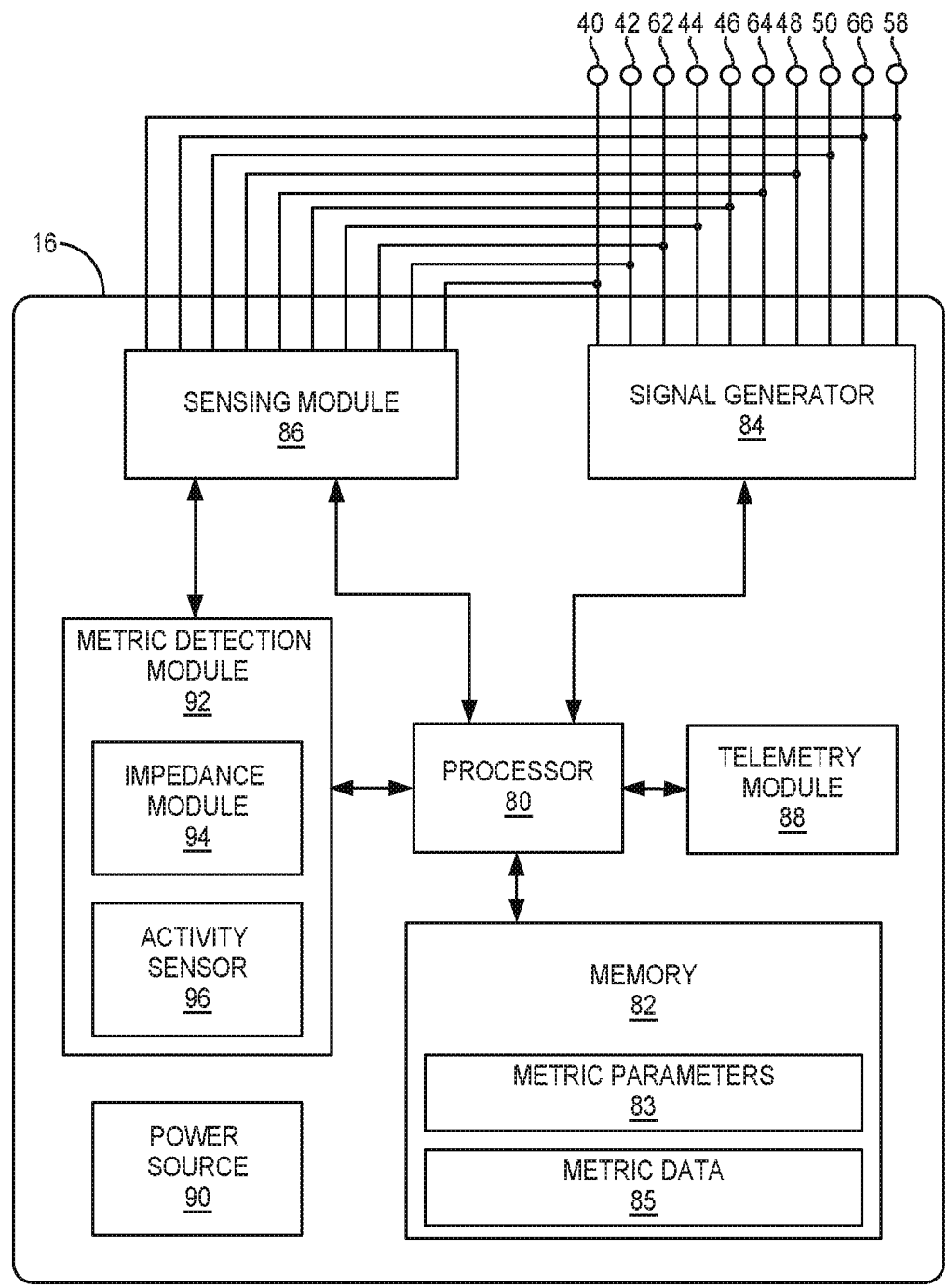
FIG. 3 is a functional block diagram of the exemplary IMD shown in FIG. 1.
Figure 4:
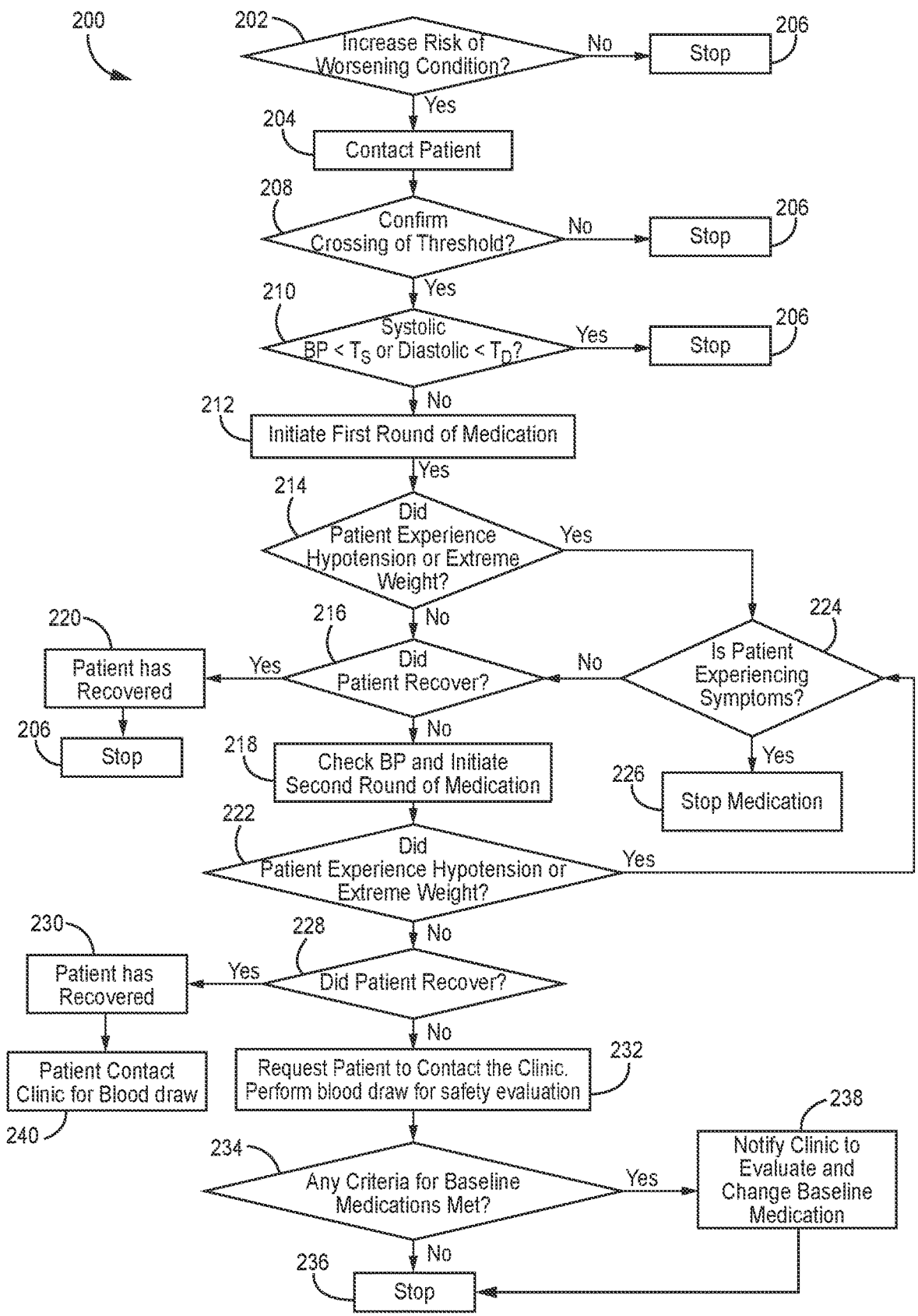
FIG. 4 is a flow diagram of an exemplary symptom management intervention process controlled by a medical system that can cause one or more adjustments to therapy that is being delivered to a patient.
Figure 5:
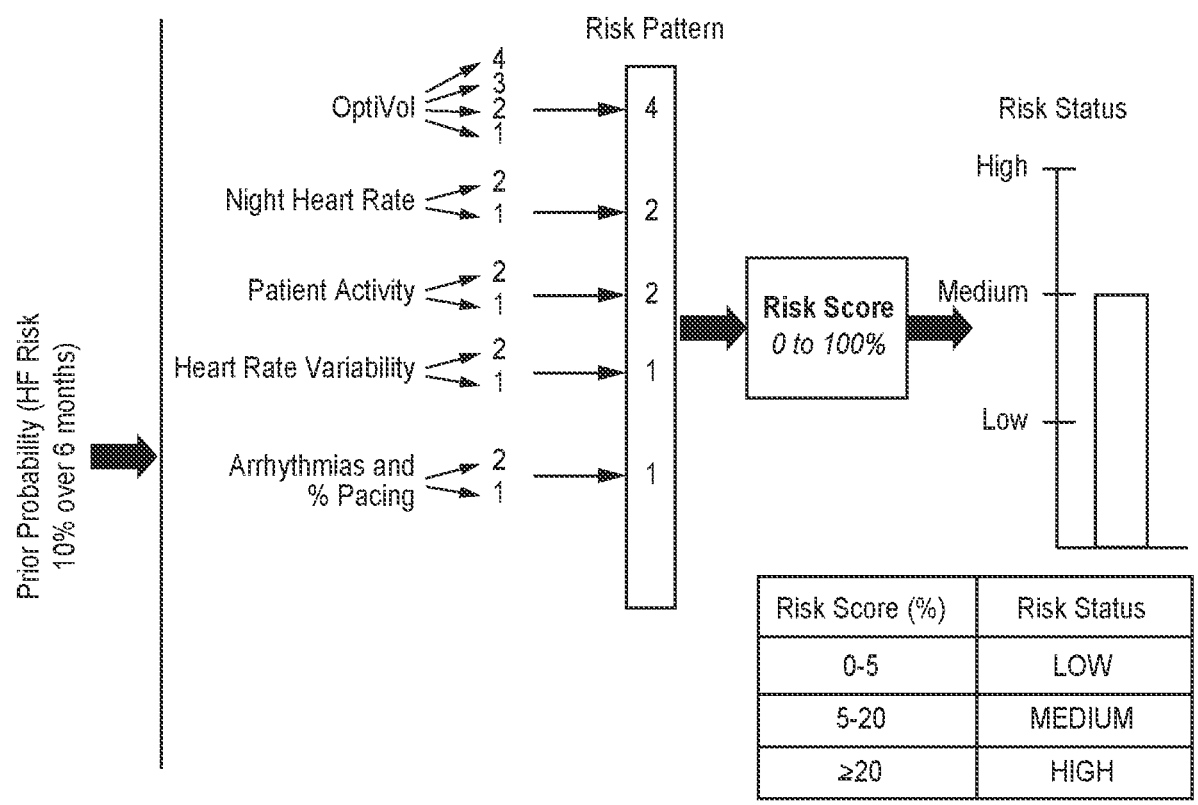
FIG. 5 is a block diagram of integrated diagnostics related to risk status.

FIGS. 1-3 disclose a system for intervening into the therapy delivered to the patient while FIG. 4 discloses a flow diagram, controlled by the system, for an intervention to modify the therapy delivered to a patient.

FIG. 1 is a block diagram illustrating an exemplary computer system 100 that can seamlessly trigger the adjustment of a patient's treatment plan without directly communicating with the patient's physician any time after the treatment plan has been sent to a centralized communication center for storage or stored into a memory of a computing device. An exemplary system is shown and described in U.S. patent application Ser. No. 15/402,839, filed on Jan. 10, 2017, the disclosure of which is incorporated herein by reference in its entirety. The treatment plan, stored at the centralized communication center or in the memory of a server, can comprise one or more rounds of medication (e.g., a first round of medication, a second round of medication etc.). Generally, adjusting treatment of the patient depends on the patient's risk of a HF event, and data acquired from IMD 16, computing devices 102a-n and/or programmer 24. A HF event is when a patient was admitted to the hospital for worsening HF or the patient has received Intravenous HF therapy (e.g. IV diuretics/vasodilators), ultrafiltration at any settings including an emergency department, ambulance, observation unit, urgent care, HF/Cardiology Clinic or the patient's home. Communication of the adjusted treatment can be delivered either electronically or via nurse to the patient.

Computer system 100 includes one or more computing devices 102a-102n, a programmer 24, a server 130, a network 110, and access point 112. Network 110 may generally be used to transmit information or data (e.g., physiological data, risk level data, recovery data) between IMD 16 to other external computing devices 102a-c. However, network 110 may also be used to transmit information from IMD 16 to an external computing device (e.g. CARELINK®). Exemplary computer systems and/or features that can implement the present disclosure include U.S. Pat. No. 8,585,604 to Bennett et al., U.S. Pat. No. 6,970,742 to Mann et al., Ritzema et al, Physician-Directed Patient Self-Management of Left Atrial Pressure in Advanced Chronic Heart Failure, Circulation, 2010, U.S. Pat. No. 7,577,475 to Cosentino et al, System, method, and apparatus for combining information from an implanted device with information from a patient monitoring apparatus, 2009, the disclosure of each are incorporated by reference in their entirety.

IMD 16 may use its telemetry module 88, described below relative to FIG. 3, to communicate with computing devices 102a-n ("n" being any whole number of computing devices), server 130, programmer 24. Typically, a wireless connection is employed. In one example of FIG. 1, access point 110, programmer 24, external device 102n, and computing devices 102a-102n can be interconnected, and able to communicate with each other, through network 112. In some cases, one or more of access point 110, programmer 24, external device 102n, and computing devices 102a-102n may be coupled to network 112 through one or more wireless connections.

Figure 7:
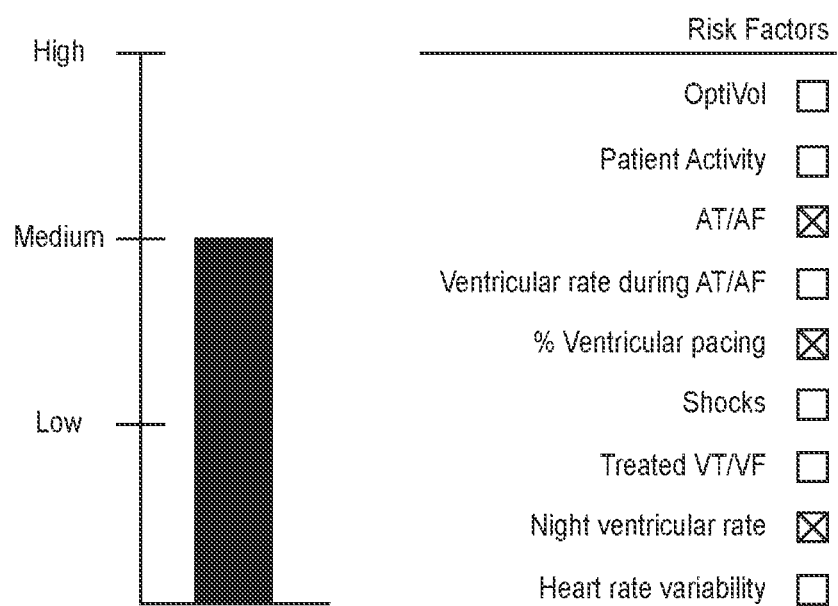
FIG. 7 depicts medium risk status relative to a set of exemplary risk factors.

Another example of a computing device 102n may be a patient's medication or drug dispenser 102, as shown in FIG. 7. The computerized drug dispenser 102 includes a set of compartments, in which each compartment 103a-d stores one or more medications at a prescribed dosage. In another embodiment, an implantable drug dispenser can be used to deliver the proper dosage of medication. Exemplary implantable drug dispensers that can be configured to include two different compartments for holding two different dosages of the same medication (e.g. diuretics, blood pressure medicine etc.). Exemplary implantable drug dispensers that can be configured to include two or more drug compartments for release into the body are shown and described in U.S. Pat. Nos. 7,001,359, 7,054,782, 7,008,413, 7,264,611, 7,160,284, all of which are incorporated by reference. In yet another embodiment, a subcutaneous drug dispenser can be used (e.g. subcutaneous implantable devices such as a drug delivery such as the Paradign Revel from MinimMed, or SC2 infuser by SC Pharmaceuticals) Implantable drug dispensers are further configured to receive communication signals to deliver the drug through a transceiver or transmitter. In one or more embodiments, the implantable drug delivery device receives a command signal from a device (server 130 computing device e.g. cell phone) from external to the device. BLUETOOTH™ technology can be used in the communication process to deliver wireless signals to the implantable drug dispensing device. The implantable drug dispenser can be configured to receive a wireless message from a computing device (e.g. Iphone™ that the user indicates through the graphical user interface to deliver a drug or the Iphone™ may use data acquired from external electrodes and/or implantable electrodes to deliver a drug or a dosage of drug different from the previously delivered dosage of drug. In one or more embodiments, the implantable drug dispenser is configured to receive command messages to adjust dosages of drug(s) delivered. In another embodiment, the implantable drug dispenser can be configured to signal another implantable medical device (LINQ™, pacemaker etc.) or external device (computing device, Iphone™) information (e.g. drug level is depleting or running very low).

The drug dispenser is further configured to receive instructions from the server to ensure that the patient has access to the correct medication and/or dosage of medication. Once the server determines a medication for a patient needs to be adjusted, the server automatically signals the computing device 102n to automatically adjust delivery of the medication. For example, assume that the patient requires a reduced dosage of a medication. The server signals the computing device 102n to adjust the dosage delivered to a patient. The computing device 102n automatically switches from the first to a second dosage compartments for drug delivery. The medication delivery device rotates from the first dosage compartment that stores a first dosage to the second dosage compartment that stores a second dosage for delivery to the patient. The medication delivery device automatically notifies the patient there has been a modification in his or her dosage. The medication delivery device then automatically notifies the patient to take the medication during the day. The drug is automatically dispensed to the patient at the proper dosage. The dispenser can be set to automatically lock drug delivery once the proper dosage has been delivered.

IMD 16, programmer 24, external device 102n, and computing devices 102a-102n may each comprise one or more processors, such as one or more microprocessors, DSPs, ASICs, FPGAs, programmable logic circuitry, or the like, that may perform various functions and operations, such as those described herein. Each processor can be configured to perform some type of analog to digital conversion (ADC) so that signals can be compared to some threshold. The signal can be filtered before or after digitizing the signal. Other applicable signal processing may also be applied.

Computing devices 102a-102n may comprise devices such as servers, computers, weight scales, portable blood pressure machines, biometric data collecting device, a computer, a symptom assessment system, a personal digital assistant (e.g. cell phone, iPad, or the like). In some examples, computing devices 102a-n may generate data that are used by server to perform any of the various functions or operations described herein, e.g., generate a heart failure risk status based on the patient metric comparisons or create patient metrics from the raw metric data. HF risk status can be calculated in a number of ways, as disclosed herein. An exemplary risk score (or risk status) is described in U.S. Provisional Application 62/554,523. Computing devices 102a-n include input/output device 104c, processor 106b and memory 108c.

Each computing device includes an input/output device 104a-c, a processor, 106a-c, and memory 108a-c. Input/output device 116 includes input devices such as a keyboard, a mouse, voice input, sensor for weight, etc. and output device includes graphical user interfaces, printers and other suitable means. Processor 106a-c or 134 includes any suitable processor. The processor 134 can be configured to perform some type of analog to digital conversion so that signal can be compared to some threshold. Processor 134 is configured to perform a variety of functions such as calculations, accessing data from memory performing comparisons, setting the start and end dates for each evaluation period etc. The evaluation period serves as an evaluation window that encompasses data, acquired from each patient, that are within the boundaries (i.e. start and end times). Exemplary calculations performed by processor 106a-c can be calculating risk of a heart failure event for each evaluation period.

Memory 108a-c may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. Memory 108a-c stores data. Exemplary data stored in memory 108a-c includes heart failure patient data, heart failure prospective risk data, intracardiac or intravascular pressure, activity, posture, respiration, thoracic impedance, impedance trend, risk of hypervolemia or hypovolemia etc. Evaluation period start and end times are also stored in memory. Heart failure patient data includes data observations (e.g. data sensed from sensors that cross a threshold). Additionally, evaluation period data is also stored in memory 108a-c. For example, the start and end dates of the evaluation period data is stored in memory 108a-c.

Programmer 24 can include any appropriate programming system, including one generally known to those skilled in the art, such as the Medtronic CARELINK™ programmer, sold by Medtronic, Plc. of Minneapolis, MN Programmer 24 may communicate wirelessly with IMD 16, such as using RF communication or proximal inductive interaction. This wireless communication is possible through the use of telemetry module, which may be coupled to an internal antenna or an external antenna. An external antenna that is coupled to programmer 24 may correspond to the programming head that may be placed over heart. The telemetry module may also be configured to communicate with another computing device via wireless communication techniques, or direct communication through a wired connection. Examples of local wireless communication techniques that may be employed to facilitate communication between programmer 24 and another computing device include RF communication according to the 102.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, programmer telemetry module (not shown) may transmit an interrogation request to telemetry module of IMD 16. Accordingly, the telemetry module may receive data (e.g. diagnostic information, real-time data related to absolute intrathoracic impedance that may be indicative of hypervolemia or hypovolemia, etc.) or diagnostic information selected by the request or based on already entered patient status to IMD 16. The data may include patient metric values or other detailed information from telemetry module of IMD 16. The data may include an alert or notification of the heart failure risk level from the telemetry module of IMD 16. The alert may be automatically transmitted, or pushed, by IMD 16 when the heart failure risk level becomes critical. In addition, the alert may be a notification to a healthcare professional, e.g., a clinician or nurse, of the risk level and/or an instruction to patient 14 to seek medical treatment (e.g. testing to confirm worsening HF etc.). In response to receiving the alert, the user interface may display the alert to the healthcare professional regarding the risk level or present an instruction to patient 14 to seek medical treatment.

Either in response to heart failure data, e.g., the risk level or patient metrics, or requested heart failure information, the user interface for a computing device or programmer 24 may present the patient metrics, the heart failure risk level, or recommended treatment (e.g. medication) to the user. In some examples, the user interface may also highlight each of the patient metrics that have exceeded the respective one of the plurality of metric-specific thresholds. In this manner, the user may quickly review those patient metrics that have contributed to the identified heart failure risk level.

Access point 110 may comprise a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein.

In another example, access point 110 may be a LINQ™ device co-located within the patient and configured to sense, record and transmit data to network 110. Alternatively, SEEQ™, configured for monitoring, may be attached to the skin of the patient. For example, SEEQ™ could be attached to the skin over the heart of the patient for cardiac monitoring. In another example, access point 110 may include a home-monitoring unit that is located within patient 14 and that may monitor the activity of IMD 16. LINQ™ and SEEQ™ commercially available from Medtronic, Inc. located in Minneapolis, MN may also be used as access point 110. An example of such a LINQ™ may be seen with respect to U.S. Pregrant Publication No. 2016-0310031 A1 filed Apr. 20, 2016, and assigned to the assignee of the present invention, the disclosure of which is incorporated by reference in its entirety herein.

Server 130 can be located at a centralized communication center such as at Cardiocom®. Server 130 is configured to perform complex computations for a large group of patients and provides secure storage in memory 136 for archival of information (e.g., patient metric data, heart failure risk levels, weight, blood pressure etc.) setup in a database 132 that has been collected and generated from IMD 16, programmer 24 and/or external devices. Exemplary medium and high risk calculations performed by server 130 (or any processor of a computing device) are shown and described in US 2016-0361026 A1 (U.S. application Ser. No. 13/391, 376) entitled METHOD AND APPARATUS FOR MONITORING TISSUE FLUID CONTENT FOR USE IN AN IMPLANTABLE CARDIAC DEVICE and US2012032243 (U.S. application Ser. No. 12/914,836 filed Oct. 28, 2010), entitled HEART FAILURE MONITORING AND NOTIFICATION, U.S. Provisional Application No. 62/554,523 filed Sep. 7, 2017 and entitled, DIFFERENTIATION OF HEART FAILURE RISK SCORES FOR HEART FAILURE MONITORING, and assigned to the assignee of the present invention, the disclosure of which is incorporated by reference in its entirety herein.

Figure 8:
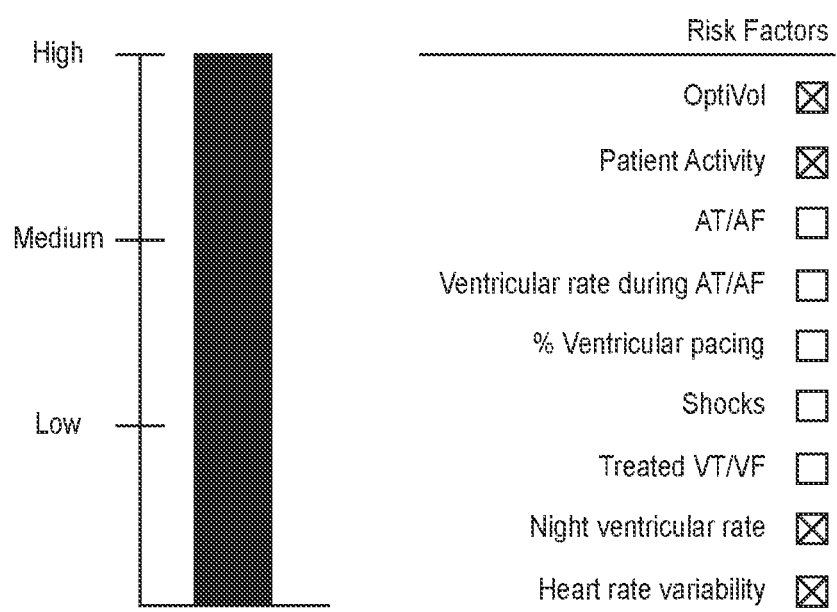
FIG. 8 depicts high risk status relative to a set of exemplary risk factors.
Figure 9:
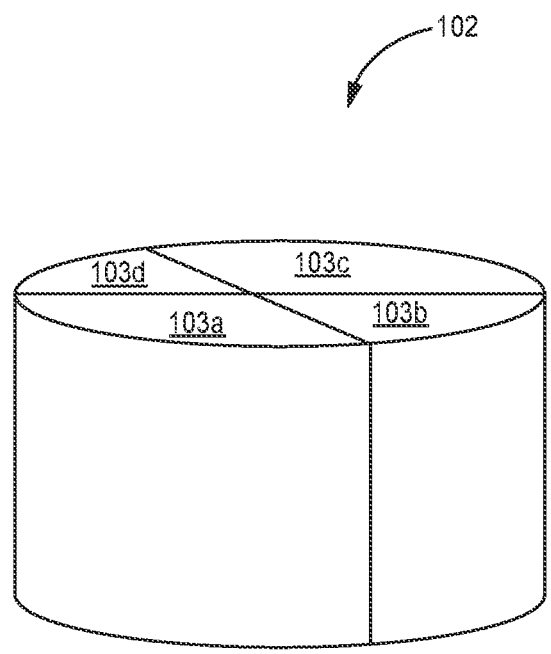
FIG. 9 is a block diagram of a patient's medication dispenser.

Examples of medium and high risk status are presented in FIGS. 7-8. Medium risk status, for example, may involve one or more conditions such as AT/AF burden exceeding a threshold value (>6 hours/day), low % V pacing and high night heart rate (>85 bpm). High risk status, for example, may involve one or more conditions such as high OptiVol™/impedance index (>60 ohm-days), patient activity (<1 hour/day), high night heart rate (>85 bpm) and low HRV (<60 ms).

Memory 136 stores a set of diagnostic metrics indicative of worsening heart failure for each patient. Diagnostic metrics or metrics can include a variety of data. Exemplary data, shown in FIG. 5, includes (1) impedance trend index commercially available in IMDs from Medtronic Plc., located in MN), (2) intrathoracic impedance, (3) atrial tachycardia/atrial fibrillation (AT/AF) burden, (4) mean ventricular rate during AT/AF, (5) patient activity, (6) ventricular (V) rate, (7) day and night heart rate, (8) percent CRT pacing, and/or (9) number of shocks. The impedance index is an indicator of the amount of fluid congestion experienced by the patient. The impedance index is the difference between an impedance measured during real time using IMD 16 and a reference impedance, that can be continuously updated, established by the IMD 16 or during another visit to the physician. The impedance index is described in greater detail with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein.

Heart rate variability (HRV) is a marker of autonomic tone and has been shown to provide prognostic information for mortality risk. A decrease in HRV is associated with increased sympathetic tone. Using HRV device diagnostic data, patients with low HRV (<100 ms) are at a higher combined risk of death and hospitalization. Patients with HRV <50 ms exhibit an even higher risk than those with HRV in the range of 50-100 ms.

Similar to HRV, elevated heart rate is a marker of elevated sympathetic tone and has been shown to have prognostic value for worsening HF. Night Heart Rate (NHR), measured between midnight and 4 AM, can be a better metric than the day time heart rate. Day time heart rate can be affected by varying activity level (e.g. rest and exercise). Patients with high NHR (75±25 bpm) typically experience higher risk of being hospitalized or dying than those who had low NHR (73±11 bpm).

Additionally, declining patient activity is associated with worsening HF status and can potentially be of value for predicting HF hospitalization. Declining patient activity can be determined by a variety of activity devices such as a FITBIT, cellphone etc.

Combination variables (e.g. combining pacing and arrhythmia related information) can also be used to evaluate worsening HF risk. For example, one of the components of combination variable is substantial decrease (>8%) in CRT pacing, which is associated with high HF events. A decline in CRT pacing can occur because of rapid conduction during AF. Thus, mean ventricular rate ≥90 bpm and atrial fibrillation (AF) burden ≥6 hours/day and shocks delivered to Ventricular Fibrillation/Ventricular Tachycardia (VT/VF) can also be components of the combination variable.

IMD 16, programmer 24, and/or computing devices a-n may communicate via wireless communication using any techniques known in the art. Examples of communication techniques may include, for example, radiofrequency (RF) telemetry, but other communication techniques such as magnetic coupling are also contemplated. In some examples, programmer 24 may include a programming head that may be placed proximate to the body of the patient near the IMD 16 implant site in order to improve the quality or security of communication between IMD 16 and programmer 24.

Network 110 may comprise a local area network, wide area network, or global network, such as the Internet. In some cases, programmer 24 or external server 130 may assemble the diagnostic data, heart failure data, prospective heart failure risk data or other suitable data in web pages or other documents for viewing by and trained professionals, such as clinicians, via viewing terminals associated with computing devices 120. The system 100 of FIG. 1 may be implemented, in some aspects, with general network technology and functionality similar to that provided by the Medtronic CareLink® Network developed by Medtronic, Plc., of Minneapolis, MN FIG. 2 is an enlarged view of IMD 16. IMD can be a leadless pacing device such as MICRA™ that is commercially available from Medtronic, Inc. located in Minneapolis, MN IMD 16 can also be a pacemaker (or ICD) coupled to leads 18, 20, and 22 and programmer 24. IMD 16 may be, for example, an implantable pacemaker, cardioverter, and/or defibrillator that provides electrical signals to heart 12 via electrodes coupled to one or more of leads 18, 20, and 22.

Patient 14 is ordinarily, but not necessarily a human patient. In general, the techniques described in this disclosure may be implemented by any medical device, e.g., implantable or external, that senses a signal indicative of cardiac activity, patient 14 activity, and/or fluid volume within patient 14. As one alternative example, the techniques described herein may be implemented in an external cardiac monitor that generates electrograms of heart 12 and detects thoracic fluid volumes, respiration, and/or cardiovascular pressure of patient 14.

Leads 18, 20, 22 extend into the heart 12 of patient 14 to sense electrical activity of heart 12 and/or deliver electrical stimulation to heart 12. Leads 18, 20, and 22 may also be used to detect a thoracic impedance indicative of fluid volume in patient 14, respiration rates, sleep apnea, or other patient metrics. Respiration metrics, e.g., respiration rates, tidal volume, and sleep apnea, may also be detectable via an electrogram, e.g., based on a signal component in a cardiac electrogram that is associated with respiration. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 100 may additionally or alternatively include one or more leads or lead segments (not shown in FIG. 2) that deploy one or more electrodes within the vena cava, or other veins. Furthermore, in some examples, system 100 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to detect intrathoracic impedance as a patient metric for identifying a heart failure risk or fluid retention levels.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for patient metrics stored in IMD 16 and/or used in generating the heart failure risk level. IMD 16 may utilize two of any electrodes carried on leads 18, 20, 22 to generate electrograms of cardiac activity. In some examples, IMD 16 may also use a housing electrode of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor heart rate (night time and day time), heart rate variability, ventricular or atrial intrinsic pacing rates, indicators of blood flow, or other indicators of the ability of heart 12 to pump blood or the progression of heart failure.

In some examples, IMD 16 may also use any two electrodes of leads 18, 20, and 22 or the housing electrode to sense the intrathoracic impedance of patient 14. As the tissues within the thoracic cavity of patient 14 increase in fluid content, the impedance between two electrodes may also change. For example, the impedance between an RV coil electrode and the housing electrode may be used to monitor changing intrathoracic impedance.

IMD 16 may use intrathoracic impedance to create a fluid index. As the fluid index increases, more fluid is being retained within patient 14 and heart 12 may be stressed to keep up with moving the greater amount of fluid. Therefore, this fluid index may be a patient metric transmitted in diagnostic data or used to generate the heart failure risk level. By monitoring the fluid index in addition to other patient metrics, IMD 16 may be able to reduce the number of false positive heart failure identifications relative to what might occur when monitoring only one or two patient metrics. Furthermore, IMD 16, along with other networked computing devices described herein, may facilitate remote monitoring of patient 14, e.g., monitoring by a health care professional when the patient is not located in a healthcare facility or clinic associated with the health care professional, during a post-hospitalization period. An example system for measuring thoracic impedance and determining a fluid index is described in U.S. Pat. No. 8,255,046 to Sarkar et al., entitled, "DETECTING WORSENING HEART FAILURE BASED ON IMPEDANCE MEASUREMENTS," which published on Feb. 4, 2010 and is incorporated herein by reference in its entirety.

Whether a patient begins to experience or is experiencing HF symptoms is based upon a variety of parameters that can change over time. Exemplary parameters capable of changing over time includes the patient's weight (i.e. extreme weight loss), hypotension, syncope, pre-syncope, all of which can be uploaded to the system 100 on a periodic basis (e.g. daily, weekly, monthly etc.) from the patient's computer and/or user device 102a-n.

FIG. 3 is a functional block diagram illustrating an example configuration of IMD 16. In the illustrated example, IMD 16 includes a processor 80, memory 82, metric detection module 92, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a therapy parameters, which may be stored in memory 82. For example, processor 80 may control signal generator 84 to deliver electrical pulses with the amplitudes, pulse widths, frequency, or electrode polarities specified by the therapy parameters.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon. Sensing may be done to determine heart rates or heart rate variability, or to detect arrhythmias or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR, CRT, and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. Processor 80 detects data (e.g. data observations etc.) at an IMD16 check and/or interrogation time point. Data is sensed based on signals from sensing module 86. Additionally, cardioversion or defibrillation shock can be determined to be needed based upon sensed data, and processor 80 may control the amplitude, form and timing of the shock delivered by signal generator 84.

Memory 82 is configured to store data. Exemplary data can be associated with a variety of operational parameters, therapy parameters, sensed and detected data, and any other information related to the therapy and treatment of patient 14. In the example of FIG. 3, memory 82 also includes metric parameters 83 and metric data 85. Metric parameters 83 may include all of the parameters and instructions required by processor 80 and metric detection module 92 to sense and detect each of the patient metrics used to generate the diagnostic information transmitted by IMD 16. Metric data 85 may store all of the data generated from the sensing and detecting of each patient metric. In this manner, memory 82 stores a plurality of automatically detected patient metrics as the data required to generate a risk level of patient 14 being admitted to the hospital due to heart failure.

Metric parameters 83 may include definitions of each of the patient metrics automatically sensed or measured by metric detection module 92. These definitions may include instructions regarding what electrodes or sensors to use in the detection of each metric. Preferred metrics include an (1) impedance trend index (also referred to as OPTIVOL® commercially available in IMDs from Medtronic Inc., located in MN), (2) intrathoracic impedance, (3) atrial tachycardia/atrial fibrillation (AT/AF) burden, (4) mean ventricular rate during AT/AF, (5) patient activity, (6) V rate, (7) day and night heart rate, (8) percent CRT pacing, and/or (9) number of shocks. Impedance trend index is described with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein. Other suitable metrics can also be used. For example, a reference or baseline level impedance is established for a patient from which subsequently acquired raw impedance data is compared. For example, raw impedance can be acquired from the electrodes (e.g. RV coil to Can) and compared to the reference impedance. Baseline impedance can be derived by averaging impedance over a duration of 7 days (1-week) to 90 days (3-months).

Metric parameters 83 may also store a metric-specific threshold for each of the patient metrics automatically detected by metric detection module 92. Metric thresholds may be predetermined and held constant over the entire monitoring of patient 14. In some examples, however, metric thresholds may be modified by a user during therapy or processor 80 may automatically modify one or more metric thresholds to compensate for certain patient conditions. For example, a heart rate threshold may be changed over the course of monitoring if the normal or baseline heart rate has changed during therapy.

In one example, these metric-specific thresholds may include a thoracic fluid index threshold of about 60 Ω-days an atrial fibrillation burden threshold of approximately 6 consecutive hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock number threshold of 1 electrical shock. These thresholds may be different in other examples, and may be configured by a user, e.g., a clinician, for an individual patient.

Processor 80 may alter the method with which patient metrics are stored in memory 82 as metric data 85. In other words, processor 80 may store the automatically detected patient metrics with a dynamic data storage rate.

Metric data 85 is a portion of memory 82 that may store some or all of the patient metric data that is sensed and/or detected by metric detection module 92. Metric data 85 may store the data for each metric on a rolling basis during an evaluation window. The evaluation window may only retain recent data and delete older data from the evaluation window when new data enters the evaluation window. In this manner, the evaluation window may include only recent data for a predetermined period of time. In one or more other embodiments, memory can be configured for long term storage of data. Processor 80 may access metric data when necessary to retrieve and transmit patient metric data and/or generate heart failure risk levels. In addition, metric data 85 may store any and all data observations, heart failure risk levels or other generated information related to the heart failure risk of patient 14. The data stored in metric data 85 may be transmitted as part of diagnostic information. Although metric parameters 83 and/or metric data 85 may consist of separate physical memories, these components may simply be an allocated portion of the greater memory 82.

Metric detection module 92 may automatically sense and detect each of the patient metrics. Metric detection module 92 may then generate diagnostic data, e.g., data that indicates a threshold has been crossed, risk levels, based on the patient metrics. For example, metric detection module 92 may measure the thoracic impedance, analyze an electrogram of heart 12, monitor the electrical stimulation therapy delivered to patient 14, or sense the patient activity. It is noted that functions attributed to metric detection module 92 herein may be embodied as software, firmware, hardware or any combination thereof. In some examples, metric detection module 92 may at least partially be a software process executed by processor 80. Metric detection module 92 may sense or detect any of the patient metrics used as a basis for generating the heart failure risk level or otherwise indication of heart failure status or that patient 14 is at risk for worsening HF. In one example, metric detection module 92 may compare each of the patient metrics to their respective metric-specific thresholds defined in metric parameters 83 to generate the heart failure risk level. Metric detection module 92 may automatically detect two or more patient metrics. In other examples, metric detection module 92 may detect different patient metrics.

In one example, metric detection module 92 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Metric detection module 92 may also analyze electrograms in conjunction with a real-time clock, patient posture or activity signal, e.g., from activity sensor 96, and/or other physiological signals indicative of when a patient is asleep or awake to determine a nighttime (or sleeping) heart rate or a daytime (or awake) heart rate or a difference between the day and night heart rate, and also analyze electrograms to determine a heart rate variability, or any other detectable cardiac events from one or more electrograms. As described above, metric detection module 92 may use peak detection, interval detection, or other methods to analyze the electrograms.

In addition, metric detection module 92 may include and/or control impedance module 94 and activity sensor 96. Impedance module 94 may be used to detect the thoracic impedance used to generate the thoracic fluid index. As described herein, impedance module 94 may utilize any of the electrodes of disclosed herein to take intrathoracic impedance measurements. In other examples, impedance module 94 may utilize separate electrodes coupled to IMD 16 or in wireless communication with telemetry module 88. Once impedance module 94 measures the intrathoracic impedance of patient 14, metric detection module 92 may generate the thoracic fluid index and compare the index to the thoracic fluid index threshold defined in metric parameters 83.

Activity sensor 96 may include one or more accelerometers or other devices capable of detecting motion and/or position of patient 14. Activity sensor 96 may therefore detect activities of patient 14 or postures engaged by patient 14. Metric detection module 92 may, for example, monitor the patient activity metric based on the magnitude or duration of each activity and compare the determined metric data to the activity threshold defined in metric parameters 83. In addition to detecting events of patient 14, metric detection module 92 may also detect certain therapies delivered by signal generator 84, e.g., as directed by processor 80. Metric detection module 92 may monitor signals through signal generator 84 or receive therapy information directly from processor 80 for the detection. Example patient metrics detected by this method may include a cardiac resynchronization therapy percentage or metrics related to delivery of electrical shocks.

The cardiac resynchronization therapy (CRT) metric may be the amount or percentage of time each day, or an amount of percentage of cardiac cycles, as examples, that IMD 16 delivers cardiac resynchronization therapy to heart 12. Low CRT amounts or percentages may indicate that beneficial therapy is not being effectively delivered and that adjustment of therapy parameters, e.g., an atrioventricular delay or a lower pacing rate, may improve therapy efficacy. In one example, higher CRT amounts or percentages may indicate that heart 12 is sufficiently pumping blood through the vasculature with the aid of therapy to prevent fluid buildup. In examples of other types of cardiac pacing (non-CRT) or stimulation therapy, higher therapy percentages may indicate that heart 12 is unable to keep up with blood flow requirements. In one or more other embodiments, low effective CRT amounts or effective V-pacing for CRT pacing can also be used as indicators of improved therapy efficacy.

An electrical shock may be a defibrillation event or other high energy shock used to return heart 12 to a normal rhythm. The metric related electrical shocks may be a number or frequency of electrical shocks, e.g., a number of shocks within a period of time. Metric detection module 92 may detect these patient metrics as well and compare them to a cardiac resynchronization therapy percentage and shock event threshold, respectively, defined in metric parameters 83 to determine when each patient metric has become critical. In one example, the electrical shock event metric may become critical when a threshold number of shocks is delivered, e.g., within a time period, or even when patient 14 even receives one therapeutic shock.

Metric detection module 92 may include additional sub-modules or sub-routines that detect and monitor other patient metrics used to monitor patient 14 and/or generate the HF risk level. In some examples, metric detection module 92, or portions thereof, may be incorporated into processor 80 or sensing module 86. In other examples, raw data used to produce patient metric data may be stored in metric data 85 for later processing or transmission to an external device. An external device may then produce each patient metric from the raw data, e.g., electrogram or raw intrathoracic impedance which is subsequently compared to a reference impedance. In other examples, metric detection module 92 may additionally receive data from one or more implanted or external devices used to detect each metric which IMD 16 may store as metric data.

In some examples, the patient metric thresholds used to generate the risk levels may change over time, e.g., the patient metric thresholds may either be modified by a user or automatically changed based on other patient conditions. Telemetry module 88 may receive commands from programmer 24, for example, to modify one or more metric parameters 83 (e.g., metric creation instructions or metric-specific thresholds). In some examples, processor 80 may automatically adjust a metric-specific threshold if certain conditions are present in patient 14. For example, the threshold may be adjusted if patient 14 is experiencing certain arrhythmias or data contained in cardiac electrograms change, e.g., there is a deviation in ST elevations or presence of pre-ventricular contractions, in such a manner that requires a change in the threshold.

Processor 80 may generate risk levels (e.g. risk of, or exhibiting hypervolemia, hypovolemia, HFH risk level) based upon the patient metrics sensed, detected, and stored in metric data 85 of memory 82. For example, processor 80 may continually update the risk level as metric detection module 92 updates each patient metric. In other examples, processor 80 may periodically update the HFH risk level according to an updating schedule. In one or more other embodiments, the total number of data observations that exceed or cross a threshold within a pre-specified period of time can be used to determine the risk of a heart failure event or worsening HF.

As described above, processor 80 may provide an alert to a user, e.g., of programmer 24, regarding the data from any patient metric and/or the HFH risk level. In one example, processor 80 may provide an alert with the HFH risk level when programmer 24 or another device communicates with IMD 16. Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Plc. of Minneapolis, MN, or some other network linking patient 14 to a clinician. In this manner, a computing device or user interface of the network may be the external computing device that delivers the alert, e.g., patient metric data. In other examples, one or more steps in the generation of the heart failure risk level may occur within a device external of patient 14, e.g., within programmer 24 ora server networked to programmer 24. In this manner, IMD 16 may detect and store patient metrics before transmitting the patient metrics to a different computing device.

System 100 controls implementation of an intervention method 200, depicted in a flow diagram of FIG. 4, to seamlessly adjust patient's therapy (e.g. medication). At block 202, a determination is made as to whether the patient is experiencing increased risk of worsening HF condition. Risk of worsening HF condition is calculated using data such as data acquired from IMD 16. For example, data, acquired from the IMD 16, shows a threshold level is crossed. The data, showing an exceedance or that a threshold has been crossed, is transmitted to server 130. Other data that may be useful for determining risk of worsening condition can be obtained from computing devices 102a-n.

Server 130 combines all of the diagnostic data in order to determine a patient's HF risk. Numerous methods exist for determining a patient's risk of experiencing a HF event. One methodology uses a Bayesian Belief Probabilistic model to categorize patients into three risk categories—low, medium and high. Exemplary medium and high risk calculations are shown and described in US2012032243, entitled HEART FAILURE MONITORING AND NOTIFICATION and assigned to the assignee of the present invention, the disclosure of which is incorporated by reference in its entirety herein. One or more other embodiments that may be employed is directed to Martin R. Cowie et al., Development and Validation Of An Integrated Diagnostic Algorithm Derived From Parameters Monitored in Implantable Devices For Identifying Patients At Risk For Heart Failure Hospitalization In An Ambulatory Setting, European Heart Journal (2013) 34, 2472-2480 doi:10.1093/eurheartj/eht083, the disclosure of which is incorporated by reference in its entirety herein. Another exemplary method and system is described in U.S. Provisional Application No. 62/554,523 filed Sep. 7, 2017, entitled, DIFFERENTIATION OF HEART FAILURE RISK SCORES FOR HEART FAILURE MONITORING, and assigned to the assignee of the present invention, the disclosure of which is incorporated by reference in its entirety herein. HF risk score algorithms may use data, acquired from signals sensed from electrodes that are associated with an implantable medical device and/or electrodes located on an external surface (e.g. skin) of the patient.

Figure 10:
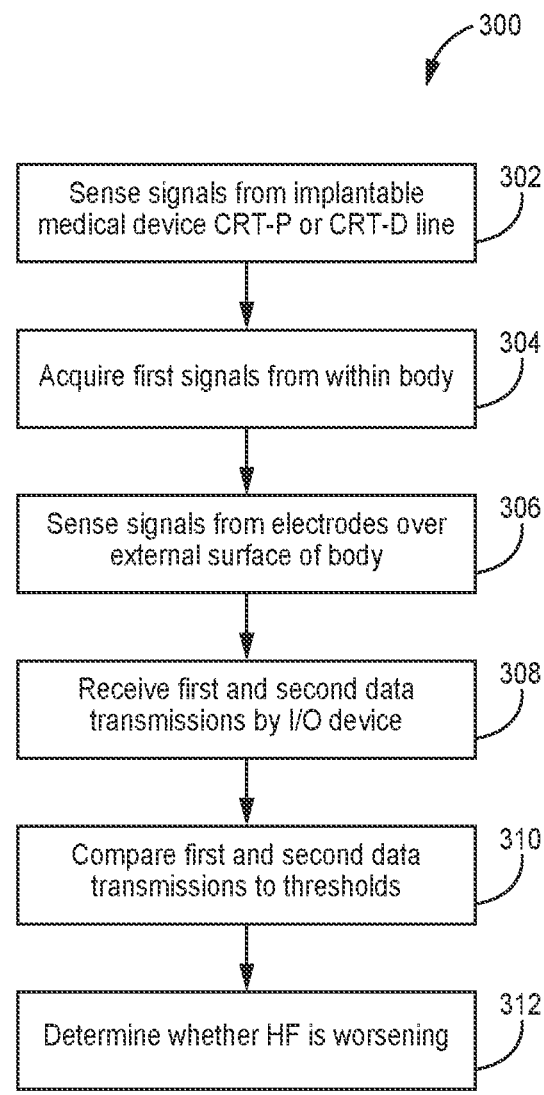
FIG. 10 is a flow diagram of an exemplary method of using data acquired from an implantable medical device and a wearable device.

FIG. 10 depicts a method 300 of using a system for managing patient therapy. The system 100 comprises an implantable medical device 16 (e.g. pacemaker, ICD, implantable monitoring device e.g. LINQ™ etc.) comprising one or more electrodes configured to be implanted within a patient's body, to acquire first signals corresponding to signals sensed at block 302 from within the patient's body and to generate first data transmissions in response to the acquired first signals at block 304. At block 306, a wearable device (e.g. watch, SEEQ™ etc.) comprising one or more electrodes configured to be positioned in contact with an external surface of the patient's body, to acquire second signals corresponding to signals sensed from the external surface of the patient's body, and to generate second data transmissions in response to the acquired second signals.

At block 308, an input/output device (104a or at server 130) is configured to receive the first data transmissions and the second data transmissions. At block 310, one or more processors (e.g. server 130, computing device, Iphone™) are configured to receive the first data transmissions and the second data transmissions. The received first data transmissions and the received second data transmissions are compared to one or more thresholds that are stored in memory. The one or more processors then compares whether data of the received first data transmissions and the received second data transmissions is indicative of a heart failure (HF) worsening episode based on the comparing. In addition, the one or more processors send a control signal to the implantable medical device (e.g. implantable drug dispenser, pacemaker etc.) to adjust a patient's therapy in response to the HF worsening episode being indicated. Adjusting patient therapy may involve a control signal from server 130 or the computing device to the implantable medical device (e.g. drug delivery, pacemaker etc.) to change a therapy parameter. For example, a dosage can be increased or decreased for a drug. In addition, or alternatively, a pacing parameter can be adjusted.

In one or more embodiments, skilled artisans understand that signals sensed from electrodes located on the skin may not be as accurate as signals that are sensed from electrodes implanted in the body and located closer to target tissue. Accordingly, the signals acquired from electrodes that are exterior to the patient's body can be weighted differently from the signals acquired from electrodes that are implanted in the patient's body. For example, data, from signals sensed from exterior electrodes, may possess up to 85% quality of data from implantable electrodes. Therefore, a correction factor of 0.85 could be applied to the data from exterior electrodes. Many examples exist of exterior electrode data and implantable electrode data. For example, a resting heart rate of 45 heart beats per minute (HBM) could be acquired from Garmin™ watch. In contrast, a resting heart rate from IMD 16 could be 50 HBM. Since IMD 16 data is presumed to be more accurate than exterior electrodes placed on the skin, the exterior electrode data can be adjusted with a correction factor to obtain HR.

An alternative approach involves a computing device, executing algorithm(s) (e.g. HF risk algorithms etc.), using data solely obtained from exterior electrodes in order to preserve the battery from IMD 16. In this example, the data obtained from exterior electrodes could have been previously compared to data obtained from more accurate implantable electrodes. The difference between the data obtained from IMD 16 and exterior electrodes is considered to be the amount of inaccuracy of the exterior electrodes and implantable electrodes. The data from exterior electrodes can be adjusted by using the amount of inaccuracy previously measured. The corrected HBM is as follows:

Resting heart rate from electrodes: [0.85*(45 HBM)+ (1.15)*50 HBM]/2=47.85 HBM. In another embodiment, data obtained from implantable devices can be weighted at about 60% while data from wearable devices can be weighted at about 40%. In yet another embodiment, data obtained from implantable devices can be weighted at about 55% while data from wearable devices can be weighted at about 45%.

Briefly, the present disclosure uses a set of variables as input. Exemplary set of variables include thoracic impedance, activity, heart rate variability, heart rate, and a combination variable based on arrhythmia and shock related information collected by the IMD 16. Intrathoracic impedance (e.g. OptiVol®) is a useful measure of a patient's HF status because HF status typically worsens when atrial filling pressure increases thereby causing retention of fluid in the pulmonary circulation. If sustained over time, fluid can infiltrate into interstitial space leading to worsening pulmonary congestion. Since blood and interstitial fluid are highly conductive, fluid accumulation in the pulmonary system leads to a reduction in thoracic impedance.

After a HF risk status of the patient is calculated, the HF risk status data is then stored into memory 136 of the server 130. If a patient's risk is deemed high, the patient automatically falls within the scope of worsening condition. Worsening HF condition also occurs in medium risk patients who exhibit sign/symptoms present (e.g. weight gain, dyspnea etc.) that may be acquired from external biometric data devices.

After evaluating patient information, a determination can be made that the risk alert from the patient is not specific to worsening HF. In this scenario, the NO path from block 202 continues from block 206 in which the method 200 is terminated and the process returns to monitoring for worsening HF conditions in the patient. The YES path continues from block 202 to block 204 in which medical personnel (e.g. nurse located a central communication center etc.) communicates with the patient through electronic communication (e.g. email, text messaging, phone call or mail) in order to determine whether the patient's worsening condition is HF related. The medical personnel may present one or more questions to the patient. For example, the patient may be asked if he or she had undergone a recent surgery. At block 208, a determination is made as to whether the threshold crossing is related to HF. A threshold crossing can be confirmed as a HF occurrence based upon information provided by the patient. Typically, to confirm whether the worsening condition is HF related, the patient is asked to respond to the questions presented below. The questions can be posed by a nurse located near the central server 130 or electronically presented to the patient via server 130 to a GUI associated with a computing device 102*a*-*n*. Exemplary questions that can be posed to a patient include the following:

1. Has the CRT-D device or lead been changed?
2. Has the patient been discharged from the hospital within the last two days?
3. Did the patient receive intravenous fluids for more than 1 day while in the hospital?
4. Did the patient experience chills, shivering, shaking or muscle aches?
5. Has the patient been treated for a chronic obstructive pulmonary disease (COPD) exacerbation?
6. Did any changes occur to baseline diuretic medication in the past 3 weeks?

If the response to anyone of the questions is "yes", the threshold crossing is deemed to not be a HF occurrence. All other occurrences may be deemed HF related.

If a threshold has been confirmed as having been crossed, the YES path continues to block 210 in which a determination associated with blood pressure (BP) will require system 100 to intervene by electronically indicating that medication should be administered to the patient. BP of the patient can be measured relative to a systolic threshold level (TS) and/or a diastolic threshold level (TD). TD and/or TS can be the typical normal threshold levels or can be individually established for each patient. A determination is made as to whether BP<TS. If BP is greater than TS, then the NO path continues to block 206 and the method 200 is terminated and the process returns to monitoring for worsening HF conditions in the patient. In contrast, if BP is greater than or equal to TS, then the NO path from block 210 to block 212 causes a first round of medication to be provided to the patient. Administration of a diuretic helps to eliminate water and may reduce blood pressure. To obtain the medication, server 130 is configured to automatically transmit a pre-authorized prescription to the patient. Alternatively, the centralized communication center staffed by a registered nurse contacts the patient to indicate that the medication at a certain dosage should be taken. The prescribed medication is stored in the home of the patient for easy access. The patient then starts taking the prescribed medication. In one embodiment, the medication is a diuretic medication (e.g. furosemide) or vasodilator (e.g. nitrate). Diuretics typically eliminate water from the patient and reduce the blood pressure.

Another determination is made at block 210 as to whether BP<TD. If BP is less than or equal to TD, then the YES path continues to block 206 and the process stops and returns to monitoring for worsening HF conditions in the patient. In contrast, if BP is greater than TD, then the NO path from block 210 to block 212 causes a first round of medication to be provided to the patient, as described above.

At block 214, a determination is made as to whether the patient is experiencing hypotension or extreme weight gain in a short period of time. If the patient is experiencing hypotension, the YES path continues to block 224 in which another determination is made as to whether the patient is experiencing HF symptoms. The YES path from block 224 continues to block 226 that causes the medication to be stopped or terminated. Medication can be stopped for a variety of conditions. Exemplary conditions include the following:

If the patient weighs less than 150 pounds, and the patient's weight changes by 3 pounds per 2 days.

If the patient weighs between 151-300 pounds, and the patient's weight changes by 4 pounds per 2 days.

if the patient weighs greater than 301 pounds, and the patient's weight changes by 5 pounds per 2 days.

One condition requires both a BP condition and the presence of a symptom, as listed immediately below. The BP condition requires the patient exhibit either a systolic blood pressure of the patient is less than 85 mmHg or a diastolic pressure of less than 40 mmHg. In addition to meeting one of the BP conditions, the patient must be experiencing a symptom that has been conveyed to medical personnel. Exemplary symptoms include (1) recent lightheadedness when moving from sitting to standing positions, or (2) muscle cramping. In addition or alternatively, the physician may customize any one of these conditions to a patient by adding or reducing the weight gain amount or blood pressure level.

Figure 6:
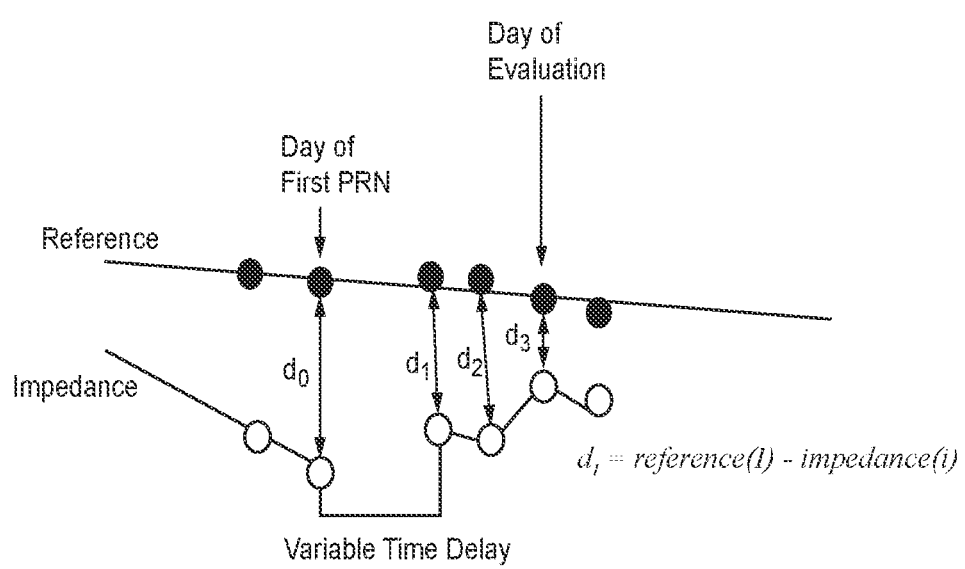
FIG. 6 is a diagram depicting exemplary recovery on a daily basis relative to a reference threshold.

The NO path from blocks 214 and 224 continue to block 216 in which a determination is made as to whether the patient has recovered from his or her worsening HF condition. Exemplary criteria for evaluating PRN efficacy in medication intervention is shown in FIG. 6. Recovery criterion is computed by the server 130 to evaluate PRN efficacy using raw intrathoracic impedance, acquired from IMD 16 associated with the patient, since impedance responds dynamically to patient volume status. Computation of recovery criterion requires the difference to be calculated between raw intrathoracic impedance and the reference impedance. Reference impedance is a component of impedance trend. Daily values for both raw and reference impedance are included with all device diagnostic transmissions spanning a duration of up to 14 months. The difference between raw and reference impedances on pre-specified time period (e.g. four day time period etc.) is required to compute recovery criterion (RC)—the day of PRN initiation ($x_0$), evaluation day ($x_3$), evaluation Day 1 ($x_2$), and evaluation Day 2 ($x_1$), recovery criterion is then computed according to the following equation:

$$RC=100*(x_0-xa)(+x_0-x_2)+(x_0-x_3))/x_0.$$

If the value of RC is greater than a threshold value of 70 (i.e. cumulative impedance recovery over the last 3 days is 70% or more from Day 0 of receiving the initial transmission), the intervention is deemed to be successful. If the value of RC is less than or equal to 70, the intervention is deemed unsuccessful and appropriate follow-up action (i.e. second PRN or notification to the investigator) is taken.

If it is determined at block 216 that the patient has recovered from his worsening HF condition, the YES path continues from block 216 to block 220 in which the patient's status of recovery is stored into memory of server 130. The process is stopped at block 206 and monitoring for worsening HF condition continues. If the patient is not experiencing a recovery, the NO path from block 216 to block 218 requires a patient's blood pressure to be checked and a second round of medication to be initiated. Typically, no additional round of medication is made beyond the second round of medication. Alternatively, a physician prescribed number N can be set of rounds medication can be administrated where N is any number from 1 to 10.

At block 218, another determination is made as to whether the patient is experiencing hypotension or extreme weight gain. The YES path continues from block 222 to block 224, as previously described. The NO path from block 222 to block 228 in which the recovery criteria, described relative to block 216, is repeated. The YES path from block 228 continues to block 230 in which the patient's status of recovery is stored into memory of server 130. The process is stopped 206 and monitoring continues for worsening HF condition.

The NO path from 228 to block 232 requires that the patient be contacted by medical personnel (e.g. nurse) so that a blood sample can be taken for evaluation and confirmation that the proper dosage of medication was provided. Block 240 also requires a blood sample be taken for evaluation and confirmation that the proper dosage of medication was provided.

At block 234, a determination is made as to whether criteria for baseline medications are met. The YES path from block 234 to block 238 requires the health clinic to evaluate and change the baseline medication, if necessary. Exemplary baseline medications along with information that may be useful for medical personnel are presented in FIGS. 13A-15B.

If changes to PRN medications are made by a physician, an updated prescription form must be electronically modified in the system 100 and records stored into memory. For example, the updated prescription by the physician can be sent (i.e. faxed, emailed) to system 100, which will automatically update the therapy.

Method 200 is stopped at block 236. Method 200 and be repeated over a pre-specified period of time designated by the user or pre-specified in a computer program executed by the processor of system 100, and/or one or more computing devices.

System 100 is configured to automatically acquire, store and analyze data from computing device(s) and, if the analyzed data indicates the patient is experiencing worsening HF, system 100 is configured to perform an activity that intervenes into the patient's therapy. Exemplary intervening activities performed by system 100 can include displaying, onto a GUI of a computing device, data (i.e. raw data and/or analyzed data), a list of options to improve the patient's health with a best option highlighted on the GUI, or automatically adjusting the patient's therapy. Data can be sensed from a variety of devices including implantable devices and/or non-implantable devices (e.g. wearable devices weight scale etc.)

The quality of the signals sensed via the electrodes positioned on non-implantable devices (e.g. wearable devices, etc.) are typically not the same as the quality of the signals sensed via the electrodes of the implantable devices for a variety of reasons. Implantable device electrodes are physically closer to the target tissue (e.g. cardiac tissue, etc.) than non-implantable electrodes and such physical proximity between the electrodes and the target tissue enables the electrodes to acquire a stronger signal. In addition, electrodes that are in close proximity to the target tissue may experience less noise compared to non-implantable electrodes. Nevertheless, non-implantable device electrodes provide information that can be useful for tracking and adjusting the patient's therapy and/or lifestyle to improve the patient's health. Generally, wearable devices can comprise one or more electrodes. Exemplary electrodes include skin electrodes, and/or optical sensors (e.g. optical heart rate sensors located on watches for placement over the wrist). Exemplary wearable devices with sensors include watches for tracking activities (e.g. Garmin FORERUNNER™, FITBIT™, Apple iWatch™) chest strap with heart sensor and/or heart rate monitor etc.). The wearable devices are configured to sense data during physical activities such as walking, running, biking, swimming or other sport activities. Exemplary health data sensed by the wearable device may include heart rate, heart rate variability, blood pressure (e.g. systolic blood pressure, diastolic blood pressure), respiration, blood oxygen saturation level etc. Wearable devices may also track inactivity (e.g. resting heart rate, sleep activity) and; in addition, distinguish between deep or light sleep activities. Health data may continue to be sensed and tracked on a twenty-four hour basis by the wearable device while the person is inactive.

In addition to data sensed via wearable electrodes (e.g. skin electrodes, etc.) other data that affects a patient's health can be sensed and monitored. For example, a patient's daily meal may be input to the device, and, if the patient is not implementing a prescribed meal plan, the patient or health care provider can be automatically alerted that the nutritional plan is not being followed. An alert can also be generated to the patient or healthcare provider to indicate supplements (e.g. vitamin or electrolyte(s)) need to be adjusted (i.e. increased or decreased). Adjusting nutrition and supplements may be important to functioning of muscles such as the heart. A patient may be determined to be outside certain requirements associated with their nutritional plan when daily designated nutritional values for the patient are not being met. For example, consuming too many foods that include high levels of sodium may cause the patient to exceed daily designated sodium limits for the patient. Too much sodium is problematic since sodium affects the patient's blood pressure. Some patients do not want to receive alerts relative to sodium. In that case, an undesired alert can be deactivated to the patient through a GUI of a computing device.

There are many ways in which food or fluid consumption can be input to server 130. For example, the patient could use a food recognition computer program on a personal digital assistant (e.g. cell phone etc.) that automatically acquires the food consumed by the patient. Exemplary methods and systems for food recognition and/or caloric data input are shown and described in U.S. Pat. No. 8,439,683 issued May 14, 2013, US 20160071431 A1 entitled FOOD DESCRIPTION PROCESSING METHODS AND APPARATUSES Al and filed on Sep. 8, 2014, incorporated by reference in their entirety. In another example, the user may input the meal consumed and estimated amount of calories through a graphical user interface (GUI) on his or her personal digital assistant (e.g. cell phone, Ipad™, computer etc.) Alternatively, the patient could take a picture of the meal. If the entire meal is not consumed, the patient may be able to adjust the amount of calories actually consumed. For example, if the user consumed only half of the meal, the user could indicate 50% of the meal was eaten and the amount of calories consumed would be automatically adjusted to indicate 50% of the calories were consumed. Alternatively, another image or picture may be taken and compared to picture taken before the food is eaten. The computer program is configured to estimate the amount of calories consumed. Another way in which the user may adjust the calories consumed involves user-input of data through a graphical user interface associated with a personal digital assistant (e.g. cellular phone, IPAD™, computer etc.).

Electrolytes (e.g. sodium (Na), magnesium (Mg) potassium (K) etc.), and other nutritional data (e.g. iron, calcium, vitamin A, vitamin C, cholesterol, protein, carbohydrates etc.) can also be acquired and stored into a memory or a database for the purpose of assisting in improving a patient's health. Electrolytes can be automatically or manually acquired by server 130. For example, the user can input the daily amount of electrolytes consumed. The daily amount of electrolytes consumed may be compared to the patient's required daily amounts electrolytes. Any daily amount of electrolyte that has not met a minimum daily amount of the daily electrolyte can cause an alert to be generated to the patient.

Alternatively, electrolytes can be automatically acquired from sensors associated with utensils, plates, bowls, containers (e.g. cups, insulated containers for water etc.). For example, utensils used for food handling (e.g. plates, forks, spoons, knifes and/or other food and liquid containers) can be configured to detect a certain amount of sodium being consumed, since sodium intake can affect blood pressure. Potassium and magnesium are also important electrolytes to automatically track since potassium and magnesium can affect muscle contraction.

After all of the data has been acquired by server 130 (or processor in the implantable medical device, portable computer etc.) can compute a dynamic risk factor. The dynamic risk factor can be calculated throughout the day or over a designated period of time (e.g. number of days). Additionally, the risk factor can be stored into memory of the implantable medical device or other computing device. The risk factor is then tracked over time to determine whether the patient's health is trending toward a worsening condition. An exemplary risk factor calculation can comprise U.S. Patent Application No. 62/554,523, entitled DIFFERENTIATION OF HEART FAILURE RISK SCORES FOR HEART FAILURE MONITORING, filed Sep. 5, 2017, incorporated in its entirety herein.

The computed risk score can be used to predict the likelihood of a cardiac event occurring within a certain period of time (e.g. the next thirty days etc.). In one or more embodiments, the computed risk factor can include a weighted sum calculation that combines data acquired from implantable and/or non-implantable electrodes. One weighted sum calculation can comprise $$X=\Sigma_{x=1}^{n}(xi*wi)/(\Sigma_{x=1}^{n}(wi)$$

in which w equals a weight, x equals a value for a parameter, "n" is a total number of values for the parameter and "i" is associated with each data. The weighted sum calculation involves (1) multiplying the numbers in a data set by each respective weight associated with the data, (2) the numbers are added from (1) (3) all of the weights are added (4) the numbers found (2) are divided by the number found in (3).

In one or more embodiments, a dynamic risk score or status calculation can have a weighted sum automatically adjusted to rely more on data acquired from one device (e.g. implantable electrodes such as subcutaneous electrodes) compared to another device (e.g. exterior electrodes). A variety of methods can be used to adjust the risk score calculation. For example, heart rate sensed by a first device (e.g. implantable device configured to sense heart rate) compared to a heart rate of a second device (i.e. wearable device) that are being sensed and are not within a threshold range of each other can cause an automatic increase of reliance on the IMD electrodes or sensors compared to the wearable device.

In one embodiment, the risk score can be dynamically calculated on a real-time basis using the most currently acquired data. The most current data can comprise any designated time period for data obtained from implantable and/or non-implantable devices. Exemplary time periods can comprise the previous 30 days, the previous week, the previous day and/or data obtained on a real-time basis.

Other embodiments contemplate adjusting the risk score using a correction factor to adjust for electrodes that may provide less reliable data. There are a number of ways to determine correction factor for non-implantable data. For example, one way of determining the correction factor may be to apply up to a 10% correction factor to non-implantable data being used in the risk computation on a real-time basis. The 10% correction factor is an estimate of the inaccuracy of the non-implantable electrodes. There are a number of examples that can be used to weight electrodes. In one embodiment, the risk score is weighted by [implantable data×0.85 (and up)+non-implantable data×0.15 (and up)] divided by the number of weighted values. In another embodiment, the risk score is weighted to daily obtained implantable data×0.90 (and up)+non-implantable data×0.10 (and up). In another embodiment, the risk score is equivalent to daily obtained implantable data×0.95 (and up)+non-implantable data×0.95 (and up). In one embodiment, the risk score is equivalent to implantable data×0.5+non-implantable data×0.5. In another embodiment, the risk score is equivalent to daily obtained implantable data×0.85 (and up)+non-implantable data×0.15 (and up).

Another method may involve customizing a patient correction factor to a particular parameter by using a very reliable method for measuring a parameter and then correlating that measurement to data acquired from wearable devices, and determining a correction factor for the wearable data to match the more reliable data. For example, watches are configured to estimate heart rate or heart rate variability using optical sensors located over the wrist. When the patient is in a health clinic, the physician may determine the patient's heart rate using a highly reliable method. For example, the doctor may determine heart rate using a noninvasive method (e.g. an echocardiogram etc.). While the heart rate or heart rate variability is being calculated using a more reliable method (e.g. implantable electrodes etc.,), the heart rate or heart rate variability can also be determined at or about the same time using the optical heart rate monitor located on the watch. The difference between the more invasive and less invasive methods for calculating heart rates can assist in determining the percent that the non-implantable device is off from the more invasive method. Even if the implantable electrodes are removed from the patient's body, the correction factor can be used with the non-implantable electrodes to estimate a more accurate heart rate. Using the estimated heart rate, a new risk score can be generated by server 130 and used to estimate the risk that the patient will need to be hospitalized within 30 days unless his or her therapies are adjusted. After obtaining a new risk score, therapy may be adjusted (e.g. increase pacing for Bradycardia pacing, decrease pacing for Tachycardia patients) and/or another type of action performed. For example, pacing can be adjusted. Pacing parameters may be modified by up to 5% from the prior pacing rate parameter. In yet another embodiment, pacing can be adjusted by up to 10%. In one or more other embodiments, medication can be automatically adjusted through an automatic drug dispenser in response to the new risk score. Prescribed medication may be limited to diuretics or other non-life-threatening medication.

In addition to dynamically calculating new risk scores, alerts can be automatically generated when acquired data indicates that a threshold is crossed and/or that the threshold is repeatedly crossed over a pre-specified period of time. For example, a significant drop or increase in heart rate or heart rate variability and/or fluid increasing over a pre-specified period of time (e.g. 24 hours) may cause an alert to be generated to the healthcare worker and/or patient that the patient is at risk of being hospitalized within a certain period of time (e.g. 1, day, 2 days, . . . up to 30 days). Other alerts may prompt the patient to perform some action. For example, a sharp increase of heart rate over a certain amount of time without increased physical activity (e.g. running etc.) may indicate that the patient may be subject to a cardiovascular event (e.g. heart attack, stroke etc.) In this scenario, the patient and/or healthcare provider would be alerted that the patient needs to go to a hospital to be evaluated by a physician for an implantable medical device and/or other therapy.

For example, threshold of electrolytes (e.g. too much sodium, potassium etc.) may be crossed. An alert may be generated to the patient or healthcare worker to indicate too much sodium has been consumed or too little potassium or water has been consumed. Regardless as to whether the patient responds to the alert, the amount of electrolytes maintained may affect the therapy that is delivered to the patient.

The data sensed by one or more sensors on and/or associated with the device (e.g. IMD, wearable device, external device etc.) can be configured to automatically transmit from the device (e.g. implantable devices, wearable devices, external devices etc.) to server 130. In addition, the device (e.g. implantable medical device) can be configured to transmit data to another device (e.g. another implantable medical device such as Medtronic's LINQ™) that then transmits the data to server 130. Server 130 then executes computer instructions to determine whether the data crosses a pre-established threshold that may be indicative of decreasing cardiovascular health, as previously described. Additionally, server 130 can be configured to track the time period in which the threshold continued to be crossed.

Many examples exist of employing data from multiple devices to perform some activity. One example of an activity performed in response to the acquired data involves adjusting therapy delivered to the patient in order to improve the patient's health. Adjusting therapy can be automatically performed by system 100, an implantable device and/or an external device. By way of illustration, an arrhythmia (e.g. atrial fibrillation (AF) etc.) can be detected via a set of electrodes that are strategically placed on devices (implantable and/or wearable devices (e.g. wearable patch, watch etc.) to obtain physiological signals (e.g. cardiac signals, etc.) in proximity to target tissue. For example, skin electrodes can be positioned over a target area. Target areas can include the wrist to obtain a pulse, on the skin over the heart, and/or on the skin over the carotid artery. Implantable devices have electrodes much closer to target tissue and obtain better quality signals than skin electrodes. After obtaining the signals from one or more sources of devices, a computing device (implantable or external) can determine whether AF is present. In response to detection of AF, drugs that are used for rhythm and/or rate control can be appropriately titrated either automatically by system 100 or manually by a health care professional (e.g. physician) reviewing an alert from system 100 and adjusting the patient's therapy via a graphical user interface (GUI) associated with a computing device and electrically coupled to system 100. Dosages of anti-platelet therapy and/or beta-blockers can be titrated using prescriptions to control ventricular rate that can be transiently elevated for the duration of AF through an automatic drug dispense. Such a strategy will be appropriate for paroxysmal and persistent AF but not for long-standing persistent AF.

In yet another example, worsening peripheral edema can be detected by an implantable device or external device (e.g. using a patch or smart sock (https://vcea.wsu.edu/eecs2016/smart-sock/) etc.). In response to detecting worsening peripheral edema, the dosage of diuretic can be adjusted appropriately through system 100 acting in an automatic way or through sending an alert to a physician to adjust the therapy. For example, a smart sock, such as a smart sock that has been developed by Washington State University, may be used to track edema via a set of sensors that monitor ankle circumference and identify increased circumference of the patient's ankle over a short period of time, which may be used as an indicator of worsening edema.

Another embodiment relates to blood pressure treatment using data obtained implantable medical device and/or wearable devices.

One or more embodiments relate to an implantable device based closed looped blood pressure control for managing hypertension (HTN). One ventricle can be paced using short AV interval (FIG. 11A) has been shown to reduce arterial blood pressure (FIG. 11B). The mechanisms involve somewhat premature ventricular contraction that result in decreased cardiac output (while still meeting the body's demand), and hence decreased blood pressure. However, the long-term pacing with short AV interval may be deleterious, and in fact may not be necessary. For example, such pacing may lead to atrial dilatation and generate a substrate for AF.

Figure 11A:
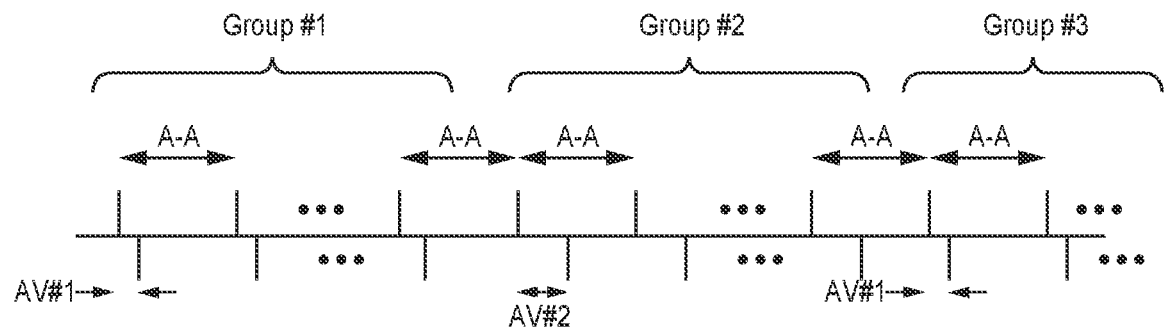
FIG. 11A depicts an HTN pacing protocol.
Figure 11B:
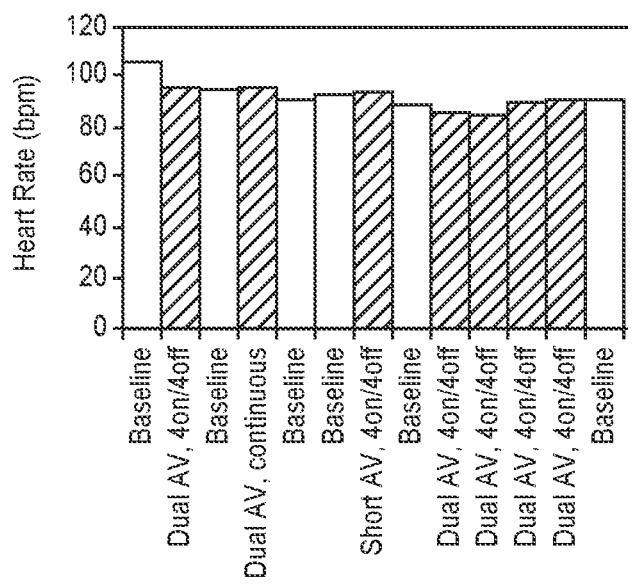
FIG. 11B shows reduction in blood pressure (second bar from left) during an HTN pacing protocol compared to control.
Figure 12:
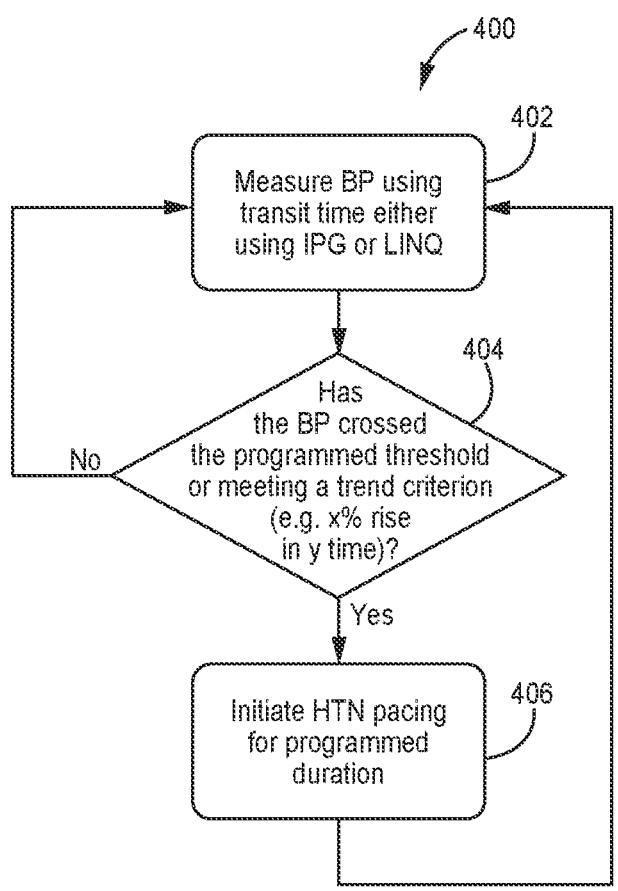
FIG. 12 is a flow diagram of an exemplary closed loop method of using a pacemaker to control blood pressure using pacing for HTN therapy and pulse transit time measurement

Referring to FIG. 11, FIG. 11A shows the hypertension (HTN) pacing protocol and FIG. 11B shows reduction in blood pressure (second bar from left) compared to control.

One embodiment involves delivering short-AV pacing in HTN patients only when necessary. To accomplish this, blood pressure will be periodically measured using pulse transit time methodology either using the pacing device (that has been modified to incorporate an optical sensor) or a LINQ™ (with optical sensor). In the latter implementation, communication between the two devices will be achieved using TCC or other methodology. Pacing therapy to manage HTN is deployed in a closed loop (FIG. 12) manner only when necessary (i.e. when BP meets set criteria) and based on the pulse transit time measurements. Specifically, whenever the pulse transit time indicates that patient's blood pressure has risen above a specified (programmable) threshold or is showing a rising trend, HTN pacing therapy is deployed (FIG. 2). Such transient increases in blood pressure may be driven by factors such as patient non-compliance with medications and other environmental factors. In the LINQ™ implementation of the device, preimplantation with LINQ can be performed to characterize BP trends in a patient and to determine whether patient is good candidate for such closed loop BP control.

EXEMPLARY EMBODIMENTS OF THE DISCLOSURE

The following embodiments are enumerated consecutively from 1 to 20 provide for various aspects of the present disclosure. In one embodiment, in a first (1) paragraph the present disclosure provides a method for determining whether to intervene with a patient's treatment, the method comprising:

Embodiment 1 is a system for managing patient therapy, the system comprising:
  (a) an implantable medical device comprising one or more electrodes configured to be implanted within a patient's body, to acquire first signals corresponding to signals sensed from within the patient's body and to generate first data transmissions in response to the acquired first signals;
  (b) a wearable device comprising one or more electrodes configured to be positioned in contact with an external surface of the patient's body, to acquire second signals corresponding to signals sensed from the external surface of the patient's body, and to generate second data transmissions in response to the acquired second signals;
  (c) an input/output device to receive the first data transmissions and the second data transmissions; and
  (d) one or more processors configured to:
    (1) receive the first data transmissions and the second data transmissions,
    (2) compare the received first data transmissions and the received second data transmissions to one or more thresholds,
    (3) determine whether data of the received first data transmissions and the received second data transmissions is indicative of a heart failure (HF) worsening episode based on the comparing, and
    (4) adjust a patient's therapy in response to the HF worsening episode being indicated.

Embodiment 2 is a system of embodiment 1 wherein the heart failure risk score is weighted such that the second data transmissions is accorded up to 85% weight compared to the first data transmissions being weighted 100%.

Embodiment 3 is a system of any of embodiments 1 or 2 wherein the heart failure risk score is weighted such that the second data transmissions is accorded up to 90% weight compared to the first data transmissions.

Embodiment 4 is a system of any of embodiments 2 or 3 wherein the heart failure risk score is weighted such that the second data transmissions is accorded up to 95% weight compared to the first data transmissions.

Embodiment 5 is a system of any of embodiments 2 or 4 wherein the heart failure risk score is weighted such that the second data transmissions is accorded less weight compared to the first data transmissions.

Embodiment 6 is a system of any of embodiments 2 or 5 wherein the heart failure risk score is weighted such that the second data transmissions is accorded less weight compared to the first data transmissions wherein fraction xi, is smaller for external electrodes compared to implanted electrodes, a weighted sum equation being $X=\Sigma_{x=1}^{n}(xi*wi)/(\Sigma_{x=1}^{n}(wi)$.

Embodiment 7 is a method for managing patient therapy, the method comprising:
  a. sensing signals from one or more electrodes associated with an implantable medical device disposed within a patient's body;
  b. acquiring first signals corresponding to the signals sensed from within the patient's body and generating first data transmissions in response to the acquired first signals;
  c. sensing signals from electrodes capable of being positioned over an external surface of the patient's body, acquiring second signals from the external surface of the patient's body and generating second data transmissions in response to the acquired second signals;
  d. receiving the first data transmissions and the second data transmissions by an input/output device;
    1. receiving the first data transmissions and the second data transmissions via one or more processors,
    2. comparing, via the one or more processors, the received first data transmissions and the received second data transmissions to one or more thresholds,
    3. determining, via the one or more processors, whether data of the received first data transmissions and the received second data transmissions is indicative of a heart failure (HF) worsening episode based on the comparing, and 4. adjusting, via the one or more processors, a patient's therapy in response to the HF worsening episode being indicated.

Embodiment 8 is a method of embodiment 7 wherein the heart failure risk score is weighted such that the second data transmissions is accorded up to 85% weight compared to the first data transmissions.

Embodiment 9 is a method of embodiments 7 or 8 wherein the heart failure risk score is weighted such that the second data transmissions is accorded up to 90% weight compared to the first data transmissions.

Embodiment 10 is a method of any of embodiments 7-9 wherein the heart failure risk score is weighted such that the second data transmissions is accorded up to 95% weight compared to the first data transmissions.

Embodiment 11 is a system for managing patient therapy, the system comprising:
 (a) an implantable medical device comprising one or more electrodes configured to be implanted within a patient's body, the one or more electrodes configured to pace tissue;
 (b) a wearable device comprising one or more electrodes configured to be positioned in contact with an external surface of the patient's body, to acquire second signals corresponding to signals sensed from the external surface of the patient's body, and to generate second data transmissions in response to the acquired second signals;
 (c) an input/output device to receive the second data transmissions; and
 (d) one or more processors configured to:
  (1) receive the second data transmissions,
  (2) compare the received second data transmissions to one or more thresholds,
  (3) determine whether data of the received second data transmissions is indicative of a heart failure (HF) worsening episode based on the comparing, and
  (4) adjust a patient's pacing therapy in response to the HF worsening episode being indicated.

Embodiment 12 is a system of embodiment 11 wherein the acquired signals are solely from one or more electrodes positioned in contact with the external surface of the patient's body.

Embodiment 13 is a system of any embodiments 11-12 wherein a battery of an implantable medical device is conserved by solely using the one or more external electrodes to acquire signals from the patient's body.

Embodiment 14 is a system of embodiments 11-13 wherein a processor external to a patient's body causes a signal to be generated to adjust therapy delivered to the patient.

Embodiment 15 is a system of any embodiments 11-14 wherein a processor external to a patient's body causes a signal to be generated to adjust therapy delivered to the patient.

Embodiment 16 is a system of any embodiments 11-15 wherein a processor, external to a patient's body, determines a patient is experiencing arrhythmia from the signals from the one or more electrodes external to the surface of the patient's body.

Embodiment 17 is a system of any embodiments 14-16 wherein the adjusted therapy comprises changing dosage of a medication.

Embodiment 18 is a system of any embodiments 14-17 wherein the adjusted therapy comprises the implantable medical device automatically changing a pacing mode.

Embodiment 19 is a system of any embodiments 14-18 wherein changing the pacing mode comprises switching between monoventricular pacing to biventricular pacing. Switching between monoventricular and biventricular pacing modes can be based on a variety of different data. Methods or systems for determining and/or automatically switching from monoventricular to biventricular pacing modes are exemplarily described and shown in U.S. Pat. No. 9,789,319, entitled SYSTEMS AND METHODS FOR LEADLESS CARDIAC REYSNCHRONIZATION THERAPY, FILED Nov. 11, 2013, U.S. Pat. No. 9,403,019, entitled ADAPTIVE CARDIAC RESYNCHRONIZATION THERAPY, filed Jan. 30, 2012, all of which are incorporated by reference in their entirety.

Embodiment 20 is a system for managing patient therapy, the system comprising:
 (e) an implantable medical device comprising one or more electrodes configured to be implanted within a patient's body and to perform one of sensing and pacing of tissue;
 (f) a wearable device comprising one or more electrodes configured to be positioned in contact with an external surface of the patient's body, to acquire second signals corresponding to signals sensed from the external surface of the patient's body, and to generate second data transmissions in response to the acquired second signals;
 (g) an input/output device to receive the first data transmissions and the second data transmissions; and
 (h) one or more processors configured to:
  (5) receive the second data transmissions,
  (6) compare the received second data transmissions to one or more thresholds,
  (7) determine whether data of the received second data transmissions is indicative of a heart failure (HF) worsening episode based on the comparing, and
  (8) adjust a pacing therapy in response to the HF worsening episode being indicated.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A system for managing patient therapy, the system comprising:
 (a) an implantable medical device comprising one or more electrodes configured to be implanted within a patient's body, to acquire first signals corresponding to one or more physiological signals sensed from within the patient's body, and to generate first data transmissions in response to the acquired first signals;
 (b) a wearable device comprising one or more electrodes configured to be positioned in contact with an external surface of the patient's body, to acquire second signals corresponding to at least one of the one or more physiological signals sensed from the external surface of the patient's body, and to generate second data transmissions in response to the acquired second signals;
 (c) an input/output device to receive the first data transmissions and the second data transmissions; and
 (d) one or more processors configured to:

(i) receive the first data transmissions and the second data transmissions,
(ii) calculate a heart failure risk score based on comparing the received first data transmissions and the received second data transmissions to one or more thresholds, and weighting the first data transmissions differently than the second data transmissions,
(iii) determine whether data of the received first data transmissions and the received second data transmissions is indicative of a heart failure worsening episode based on the heart failure risk score, and
(iv) display one of an indication of the heart failure worsening episode or the heart failure risk score on a graphical user interface of a computing device in response to the heart failure worsening episode being detected.

2. The system of claim 1 wherein the heart failure risk score is weighted such that the second data transmissions is accorded up to 85% weight compared to the first data transmissions being weighted 100%.

3. The system of claim 1 wherein the heart failure risk score is weighted such that the second data transmissions is accorded up to 90% weight compared to the first data transmissions.

4. The system of claim 1 wherein the heart failure risk score is weighted such that the second data transmissions is accorded up to 95% weight compared to the first data transmissions.

5. The system of claim 1 wherein the heart failure risk score is weighted such that the second data transmissions is accorded less weight compared to the first data transmissions.

6. A method for managing patient therapy, the method comprising:
  a. sensing one or more physiological signals from one or more electrodes associated with an implantable medical device disposed within a patient's body;
  b. acquiring first signals corresponding to the one or more physiological signals sensed from within the patient's body and generating first data transmissions in response to the acquired first signals;
  c. sensing at least one of the one or more physiological signals from electrodes capable of being positioned over an external surface of the patient's body, acquiring second signals from the external surface of the patient's body and generating second data transmissions in response to the acquired second signals;
  d. receiving the first data transmissions and the second data transmissions by an input/output device;
  e. receiving the first data transmissions and the second data transmissions via one or more processors,
  f. calculating a heart failure risk score based on comparing, via the one or more processors, the received first data transmissions and the received second data transmissions to one or more thresholds and weighting the first data transmissions differently than the second data transmissions,
  g. determining, via the one or more processors, whether data of the received first data transmissions and the received second data transmissions is indicative of a heart failure worsening episode based on the heart failure risk score, and
  h. adjusting, via the one or more processors, a patient's therapy in response to the heart failure worsening episode being determined.

7. The method of claim 6 wherein the heart failure risk score is weighted such that the second data transmissions is accorded up to 85% weight compared to the first data transmissions.

8. The method of claim 6 wherein the heart failure risk score is weighted such that the second data transmissions is accorded up to 90% weight compared to the first data transmissions.

9. The method of claim 6 wherein the heart failure risk score is weighted such that the second data transmissions is accorded up to 95% weight compared to the first data transmissions.

10. The method of claim 6 wherein the heart failure risk score is weighted such that the second data transmissions is accorded less weight compared to the first data transmissions.

* * * * *